(12) United States Patent
Abagyan et al.

(10) Patent No.: US 11,919,880 B2
(45) Date of Patent: Mar. 5, 2024

(54) HCV PROTEASE INHIBITORS

(71) Applicant: The Regents of the University of California, Oakland, CA (US)

(72) Inventors: Ruben Abagyan, San Diego, CA (US); Ittipat Meewan, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 17/489,309

(22) Filed: Sep. 29, 2021

(65) Prior Publication Data
US 2022/0106290 A1    Apr. 7, 2022

Related U.S. Application Data

(60) Provisional application No. 63/086,946, filed on Oct. 2, 2020.

(51) Int. Cl.
*C07D 401/12* (2006.01)
*A61P 31/14* (2006.01)
*C07D 209/20* (2006.01)

(52) U.S. Cl.
CPC ............ *C07D 401/12* (2013.01); *A61P 31/14* (2018.01); *C07D 209/20* (2013.01)

(58) Field of Classification Search
CPC ............................ C07D 209/20; C07D 401/12
See application file for complete search history.

(56) References Cited

PUBLICATIONS

Meewan, et al. ACS Omega 2019, 4, 16999-17008.*
Lacivita, et al. Bioorg. Med. Chem. 25 (2017) 277-292.*
Urea [online] retrieved from the internet on May 27, 2023. URL https://pubchem.ncbi.hlm.nih.gov/compound/urea.*

* cited by examiner

*Primary Examiner* — Shawquia Jackson
(74) *Attorney, Agent, or Firm* — SCHWEGMAN LUNDBERG & WOESSNER, P.A.

(57) ABSTRACT

Hepatitis C virus (HCV) is a human pathogen with high morbidity. The HCV NS3/4A protease is essential for viral replication and is one of top three drug targets. A number of drugs have been developed but drug resistant mutant strains emerged. Here we screened and synthesized of novel class of small molecules of Formula I or Formula IA based on tryptophan derivative scaffold as HCV NS3/4A protease inhibitors that is active against both wild type and mutant form of the protease. Only the docking hits with a binding pose that is not affected by the most frequent mutations in the active site were selected for experimental validation. The antiviral activities were evaluated by replicon and enzymatic assays. Twenty-two compounds in this series were found to inhibit HCV with $EC_{50}$ values ranging between 0.64 to 63 μM with compound 22 being the most active of this series. In protease assays, 22 had a comparable inhibition profile for the common mutant HCV GT1b D168A and the wild type enzyme. However, in the same assay, potency of the approved drug, Simeprevir, decreased 5.7-fold for the mutant enzyme relative to the wild-type. The top three inhibitors were also tested against four human serine proteases and were shown to be specific to the viral protease. The fluorescent based cell viability assay demonstrated a sufficient therapeutic range for the top three candidates.

6 Claims, 8 Drawing Sheets

HCV PROTEASE INHIBITORS

This application claims the benefit of priority to U.S. Provisional Patent Application No. 63/086,946 filed on Oct. 2, 2020, which application is incorporated in its entirety as if fully set forth herein.

BACKGROUND

An estimated 170 million people around the world are infected with hepatitis C virus (HCV). HCV is transmitted through patient exposure to infected blood. Without treatment, chronic HCV infection can cause serious liver disease including cirrhosis and hepatocellular carcinoma. According to the World Health Organization record, approximately 400,000 deaths occur annually due to HCV-related complications making it a serious health threat[1-2]. The nonstructural proteins of HCV play important roles in the viral production and replication. Three viral proteins, namely NS3/4A serine protease, NS5A IFN-resistance protein, and NS4B polymerase, are the major drug targets for the existing anti-viral therapeutics[25].

The NS3/4A protease is responsible for selective cleavage of polyproteins into individual viral proteins (NS4A, NS4B, NS5A, and NS5B)[12]. The first NS3/4A HCV protease inhibitors, boceprevir and telaprevir, approved in 2011, were prescribed to patients with genotype 1 (GT1) viral strain. In general, HCV infected patients are treated for 24 to 48 weeks with a cocktail containing a protease inhibitor, pegylated interferon alpha (PEG-IFNα) and ribavirin (RBV). A second generation of orally available NS3/4 HCV protease inhibitor simeprevir (Olysio, Sovriad) and nucleoside analogue NS5B polymerase inhibitor sofosbuvir (Sovaldi) received FDA approval in 2013[5,13]. Between 2013-2016, several noncovalent peptidomimetic protease inhibitors including linear (asunaprevir), $P_1$-$P_3$ macrocyclic compounds (danoprevir, simeprevir, paritaprevir), and $P_2$-$P_4$ macrocycle compounds (vaniprevir, grazoprevir) were also approved in combination with NS5A interferon resistance inhibitor and/or NS5B polymerase inhibitor. For these inhibitors, $P_1$. $P_2$. $P_3$ and $P_4$ corresponds to the amino acid positions of the inhibitor that interacts with the $S_1$, $S_2$. $S_3$ and $S_4$ substrate binding pockets of the protease, respectively.

There are six well characterized HCV genotypes (GT1-GT6) and the $P_2$-$P_4$ macrocycle compounds have broad cross-genotype specificity[1]. GT1 is the most studied and targeted genotype[4], however several common mutants of the HCV protease have emerged that include Q80K/R, R123K, R155K/Q, 156T, D168A/V/G and 1170T. These mutations are located in the $S_2$ and $S_4$ pockets[30,31,35] and have led to drug-resistance. Several studies have shown that these single amino acid substitutions confer the resistance to all linear, $P_1$-$P_3$ macrocyclic, and $P_2$-$P_4$ macrocycle compounds[7,16-19]. The most prevalent mutants are D168A and R155K[40].

SUMMARY

The present disclosure provides in one embodiment a compound according to Formula I or a pharmaceutically acceptable salt thereof:

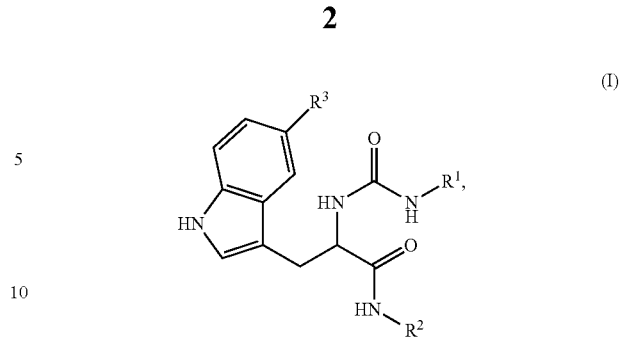

In Formula I, $R^1$ is $C_6$-$C_{10}$-aryl optionally substituted by one or more substituents independently selected from the group consisting of $C_1$-$C_6$-alkyl, $C_1$-$C_6$-alkoxy, —S($C_1$-$C_6$-alkyl), halo, —OH, —NO$_2$, —NRR', —C(O)OR.

$R^2$ is —(CH$_2$)$_m$(NH)$_n$($C_6$-$C_{10}$-aryl), —(CH$_2$)$_m$(NH)$_n$-(3- to 14-membered heterocycloalkyl) (wherein 1-4 ring members are independently selected from N, O, and S), —(CH$_2$)$_m$(NH)$_n$—($C_3$-$C_{14}$-cycloalkyl), and -(3- to 14-membered heterocycloalkyl)-($C_6$-$C_{10}$-aryl), wherein 1-4 ring members in heterocycloalkyl are independently selected from N, O, and S; wherein each aryl, heterocycloalkyl, and cycloalkyl are optionally substituted by one or more substituents independently selected from the group consisting of $C_1$-$C_6$-alkyl, $C_1$-$C_6$-alkoxy, —OH, —NRR', and C(O)OR;

$R^3$ is selected from the group consisting of H, $C_1$-$C_6$-alkyl, $C_1$-$C_6$-alkoxy, halo, and —OH;

R and R' are independently selected from H and $C_1$-$C_6$-alkyl;

m is an integer selected from 1, 2, and 3; and n is an integer selected from 0 and 1.

In another embodiment, the disclosure provides a pharmaceutical composition comprising a compound as disclosed herein or pharmaceutically acceptable salt thereof and a pharmaceutically acceptable carrier.

In still another embodiment, the disclosure provides a method for treating hepatitis C virus in a subject suffering therefrom, comprising administering to the subject a therapeutically effective amount of a compound as disclosed herein or pharmaceutically acceptable salt thereof.

In this study, we used computational modeling, docking, cell-based assays and enzymatic assays to identify compounds that inhibit both the wild-type NS3/4A protease and the D168A mutant. This was achieved by optimizing the binding efficiency to $S_1$ and $S_3$ pockets within HCV NS3/4 protease active site and avoiding $S_2$ and $S_4$ pockets used by the current drugs and susceptible to mutations. The screening, identification, synthesis, and activity validation of compounds from the UC San Diego CDIPD library against the GT1 wild-type virus and the HCV protease D168A virus resulted in new promising candidates with desired properties.

DETAILED DESCRIPTION

Figure 1:
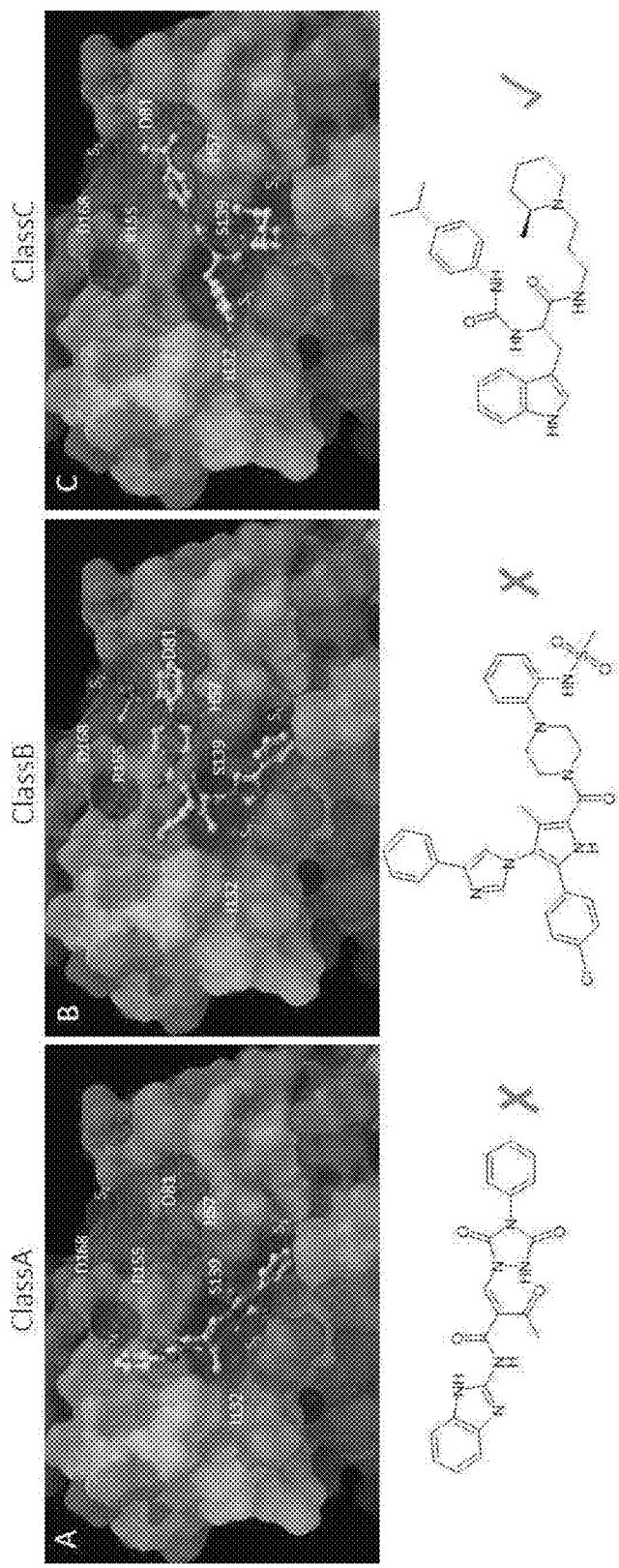
FIG. 1. Binding pose of compound that belong to (A) class A (B) class B, and (C) class C (white) in the HCV GT1a NS3/4A crystal structure represented by multicolor skin (PDB code 5EQR)[24]. Binding mode from class A and class B have some attraction interaction in drug resistance susceptible sub-pocket $S_2$ and $S_4$ while class C compounds show preferred interaction with the receptor.
Figure 2:
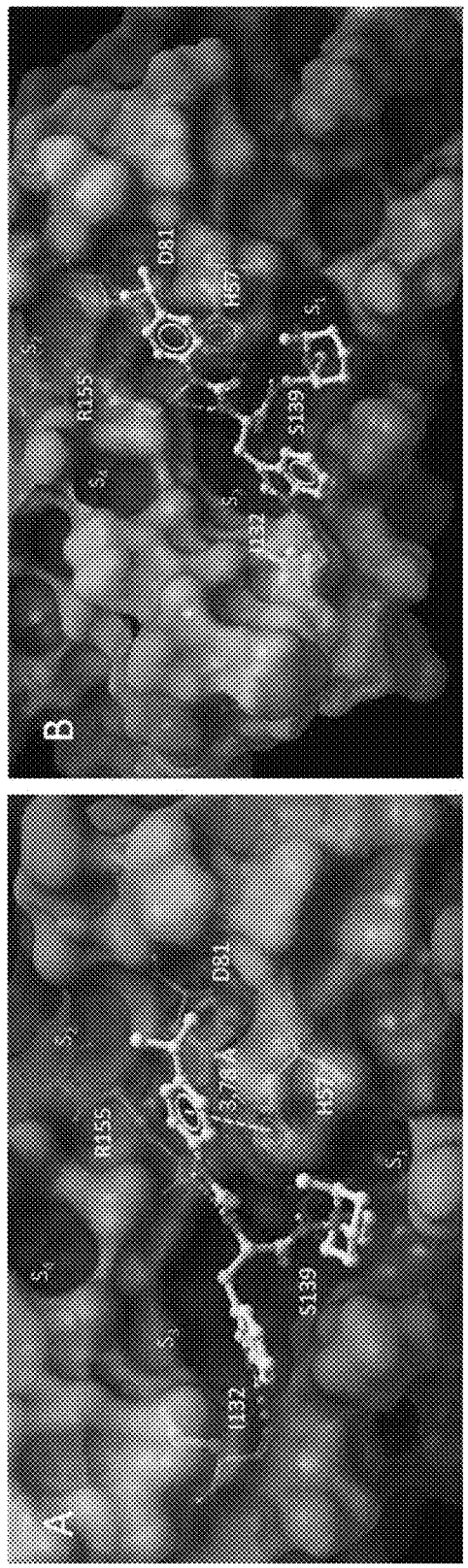
FIG. 2. Structural modelling of compound 12 in HCV NS3/4A active site. (A) Binding mode of 5 (light yellow) in the HCV GT1a NS3/4A crystal structure represented by multicolor skin (PDB code 5EQR)[24]. Compound 12 is occupied in $S_1$ and $S_3$ pockets and forming hydrogen bond interactions (green) with Arg155, 1132 (pink), hydrogen bonding interactions are shown as dashed green and orange lines. (B) Pi-stacking interaction (dashed yellow) between isopropylphenyl group of 12 and His57 (pink) with the distance of 3.78 Å

The present disclosure relates in part to computational modeling, docking, cell-based assays and enzymatic assays to identify compounds that inhibit both the wild-type NS3/4A protease and the D168A mutant. This was achieved by optimizing the binding efficiency to $S_1$ and $S_3$ pockets within HCV NS3/4 protease active site and avoiding $S_2$ and $S_4$ pockets used by the current drugs and susceptible to mutations.

Definitions

"Alkyl" refers to straight or branched chain hydrocarbyl including from 1 to about 20 carbon atoms. For instance, an alkyl can have from 1 to 10 carbon atoms or 1 to 6 carbon atoms. Exemplary alkyl includes straight chain alkyl groups such as methyl, ethyl, propyl, butyl, pentyl, hexyl, heptyl, octyl, nonyl, decyl, undecyl, dodecyl, and the like, and also includes branched chain isomers of straight chain alkyl groups, for example without limitation, —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH 3)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$) 2, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, and the like. Thus, alkyl groups include primary alkyl groups, secondary alkyl groups, and tertiary alkyl groups. An alkyl group can be unsubstituted or optionally substituted with one or more substituents as described herein below.

The phrase "substituted alkyl" refers to alkyl substituted at one or more positions, for example, 1, 2, 3, 4, 5, or even 6 positions, which substituents are attached at any available atom to produce a stable compound, with substitution as described herein. "Optionally substituted alkyl" refers to alkyl or substituted alkyl.

Each of the terms "halogen," "halide," and "halo" refers to —F or fluoro, —Cl or chloro, —Br or bromo, or —I or iodo.

The term "alkoxy" refers to an —O-alkyl group having the indicated number of carbon atoms. For example, a (C$_1$-C$_6$)alkoxy group includes —O-methyl, —O-ethyl, —O-propyl, —O— isopropyl, —O-butyl, —O-sec-butyl, —O-tert-butyl, —O-pentyl, —O-isopentyl, —O-neopentyl, —O— hexyl, —O-isohexyl, and —O-neohexyl.

The term "cycloalkyl" refers to a saturated monocyclic, bicyclic, tricyclic, or polycyclic, 3- to 14-membered ring system. The cycloalkyl may be attached via any atom. Representative examples of cycloalkyl include, but are not limited to cyclopropyl, cyclobutyl, cyclopentyl, cyclohexyl. A cycloalkyl group can be unsubstituted or optionally substituted as described herein.

"Aryl" when used alone or as part of another term means a carbocyclic aromatic group, optionally fused, having the number of carbon atoms designated or if no number is designated, up to 14 carbon atoms, such as a C$_6$-C$_{14}$-aryl. Particular aryl groups are phenyl, naphthyl, biphenyl, phenanthrenyl, naphthacenyl, and the like (see e.g. *Lang's Handbook of Chemistry* (Dean, J. A., ed) 13$^{th}$ ed. Table 7-2 [1985]). A particular aryl is phenyl. "Aryl" can be optionally fused with a cycloalkyl ring, as herein defined. An aryl group can be unsubstituted or optionally substituted with one or more substituents as described herein.

The term "heteroatom" refers to N, O, and S. Compounds of the present disclosure that contain N or S atoms can be optionally oxidized to the corresponding N-oxide, sulfoxide, or sulfone compounds.

"Heterocycloalkyl" means a saturated or partially unsaturated non-aromatic monocyclic, bicyclic, tricyclic or polycyclic ring system that has from 3 to 14, such as 3 to 6, atoms in which from 1 to 3 carbon atoms in the ring are replaced by heteroatoms of O, S or N. A heterocycloalkyl is optionally fused with aryl or heteroaryl of 5-6 ring members, and includes oxidized S or N, such as sulfinyl, sulfonyl and N-oxide of a tertiary ring nitrogen. The point of attachment of the heterocycloalkyl ring is at a carbon or heteroatom such that a stable ring is retained. Examples of heterocycloalkyl groups include without limitation morpholino, tetrahydrofuranyl, dihydropyridinyl, piperidinyl, pyrrolidinyl, piperazinyl, dihydrobenzofuryl, and dihydroindolyl. A heterocycloalkyl group can be unsubstituted or optionally substituted with one or more substituents as described herein.

The substituent —CO$_2$H may be replaced with bioisosteric replacements such as:

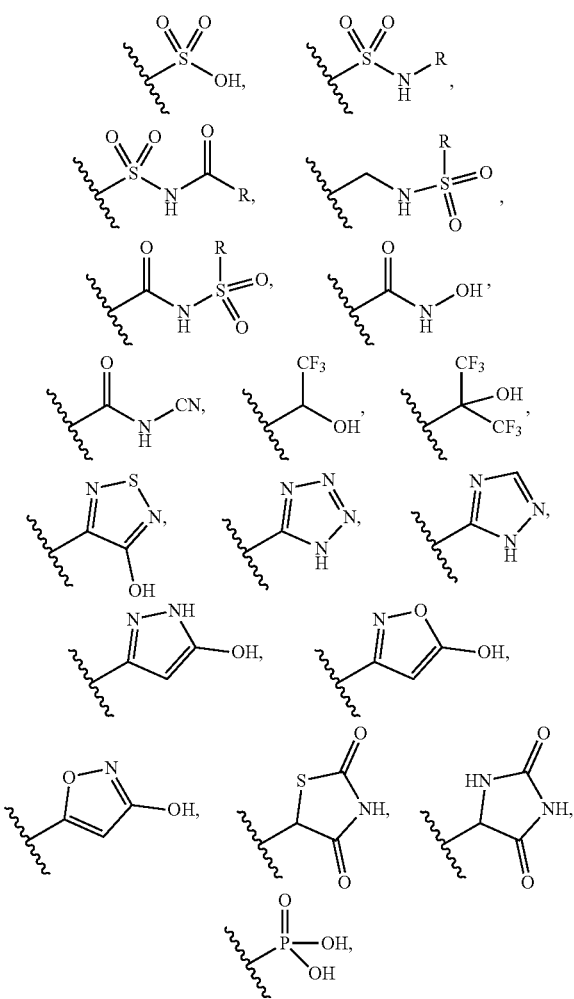

and the like, wherein R has the same definition as R$^4$ as defined herein. See, e.g., THE PRACTICE OF MEDICINAL CHEMISTRY (Academic Press: New York, 1996), at page 203.

Compounds described herein can exist in various isomeric forms, including configurational, geometric, and conformational isomers, including, for example, cis- or trans-conformations. The compounds may also exist in one or more tautomeric forms, including both single tautomers and mixtures of tautomers. The term "isomer" is intended to encompass all isomeric forms of a compound of this disclosure, including tautomeric forms of the compound. The compounds of the present disclosure may also exist in open-chain or cyclized forms. In some cases, one or more of the cyclized forms may result from the loss of water. The specific composition of the open-chain and cyclized forms may be dependent on how the compound is isolated, stored or administered. For example, the compound may exist primarily in an open-chained form under acidic conditions but cyclize under neutral conditions. All forms are included in the disclosure.

Some compounds described herein can have asymmetric centers and therefore exist in different enantiomeric and diastereomeric forms. A compound as described herein can be in the form of an optical isomer or a diastercomer. Accordingly, the disclosure encompasses compounds and their uses as described herein in the form of their optical isomers, diastereoisomers and mixtures thereof, including a racemic mixture. Optical isomers of the compounds of the disclosure can be obtained by known techniques such as asymmetric synthesis, chiral chromatography, simulated moving bed technology or via chemical separation of stereoisomers through the employment of optically active resolving agents.

Unless otherwise indicated, the term "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound. The stereoisomer as described above can be viewed as composition comprising two stereoisomers that are present in their respective weight percentages described herein.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

In this description, a "pharmaceutically acceptable salt" is a pharmaceutically acceptable, organic or inorganic acid or base salt of a compound described herein. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2- naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

The terms "prevent," "preventing," and "prevention" refer to the prevention of the onset, recurrence, or spread of the disease in a patient resulting from the administration of a prophylactic or therapeutic agent.

The term "effective amount" refers to an amount of a compound as described herein or other active ingredient sufficient to provide a therapeutic or prophylactic benefit in the treatment or prevention of a disease or to delay or minimize symptoms associated with a disease. Further, a therapeutically effective amount with respect to a compound as described herein means that amount of therapeutic agent alone, or in combination with other therapies, that provides a therapeutic benefit in the treatment or prevention of a disease. Used in connection with a compound as described herein, the term can encompass an amount that improves overall therapy, reduces or avoids symptoms or causes of disease, or enhances the therapeutic efficacy of or is synergistic with another therapeutic agent.

A "patient" or subject" includes an animal, such as a human, cow, horse, sheep, lamb, pig, chicken, turkey, quail, cat, dog, mouse, rat, rabbit or guinea pig. In accordance with some embodiments, the animal is a mammal such as a non-primate and a primate (e.g., monkey and human). In one embodiment, a patient is a human, such as a human infant, child, adolescent or adult. In the present disclosure, the terms "patient" and "subject" are used interchangeably.

The present disclosure provides in one embodiment a compound according to Formula I or a pharmaceutically acceptable salt thereof:

(I)

In Formula I, $R^1$ is $C_6$-$C_{10}$-aryl optionally substituted by one or more substituents independently selected from the group consisting of $C_1$-$C_6$-alkyl, $C_1$-$C_6$-alkoxy, —S($C_1$-$C_6$-alkyl), halo, —OH, —NO$_2$, —NRR', —C(O)OR.

$R^2$ is —(CH$_2$)$_m$(NH)$_n$—(C$_6$-C$_{10}$-aryl), —(CH$_2$)$_m$(NH)$_n$-(3- to 14-membered heterocycloalkyl) (wherein 1-4 ring members are independently selected from N, O, and S), —(CH$_2$)$_m$(NH)$_n$—(C$_3$-C$_{14}$-cycloalkyl), and -(3- to 14-membered heterocycloalkyl)-(C$_6$-C$_{10}$-aryl), wherein 1-4 ring members in heterocycloalkyl are independently selected from N, O, and S; wherein each aryl, heterocycloalkyl, and cycloalkyl are optionally substituted by one or more substituents independently selected from the group consisting of $C_1$-$C_6$-alkyl, $C_1$-$C_6$-alkoxy, —OH, —NRR', and C(O)OR;

$R^3$ is selected from the group consisting of H, $C_1$-$C_6$-alkyl, $C_1$-$C_6$-alkoxy, halo, and —OH;

R and R' are independently selected from H and $C_1$-$C_6$-alkyl;

m is an integer selected from 1, 2, and 3; and n is an integer selected from 0 and 1.

In some embodiments, the compound of Formula I is a compound of Formula IA:

(IA)

or a pharmaceutically acceptable salt thereof.

In some embodiments, the disclosure provides a compound or pharmaceutically acceptable salt thereof according to Formula I or Formula IA wherein $R^1$ is optionally substituted phenyl; $R^2$ is —(CH$_2$)$_m$(NH)$_n$-(3- to 14-membered heterocycloalkyl) or —(CH$_2$)$_m$(NH)$_n$—(C$_3$-C$_4$-cycloalkyl); m is 3; and n is 0.

In exemplary embodiments, $R^1$ is optionally substituted phenyl; and $R^2$ is

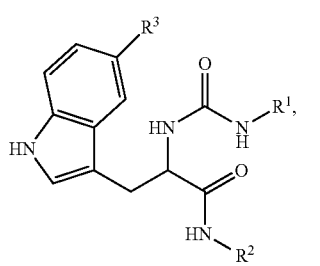

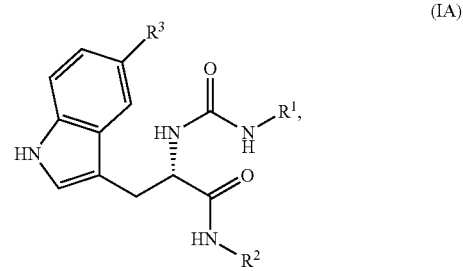

Specific examples of Formula I and Formula IA compounds are summarized in the following Table 1:
| Compound | R¹ | R² | R³ |
|---|---|---|---|
| 1 | 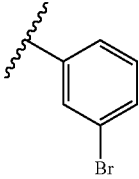 [SMILES: *c1cccc(Br)c1] | 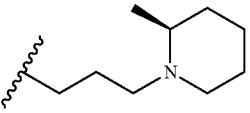 [SMILES: *CCCN1CCCC[C@@H]1C] | H |
| 2 | 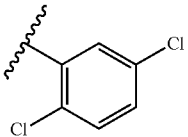 [SMILES: *c1cc(Cl)ccc1Cl] | 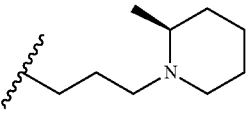 [SMILES: *CCCN1CCCC[C@@H]1C] | F |
| 3 | 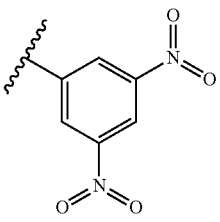 [SMILES: *c1cc([N+](=O)[O-])cc([N+](=O)[O-])c1] | 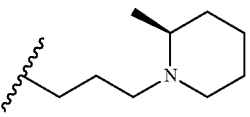 [SMILES: *CCCN1CCCC[C@@H]1C] | H |
| 4 | 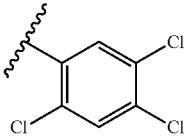 | 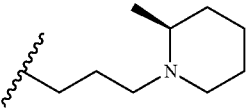 [SMILES: *CCCN1CCCC[C@@H]1C] | H |
| 5 | 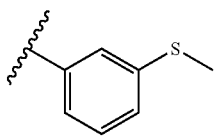 [SMILES: *c1cccc(SC)c1] | 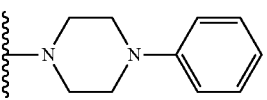 | H |
| 6 | 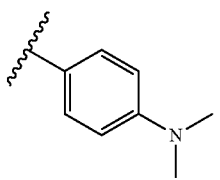 [SMILES: *c1ccc(N(C)C)cc1] | 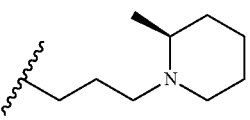 [SMILES: *CCCN1CCCC[C@@H]1C] | H |
| 7 | 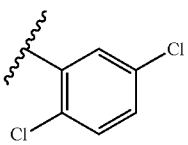 | 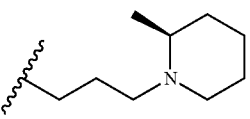 [SMILES: *CCCN1CCCC[C@@H]1C] | CH₃ |
| 8 | 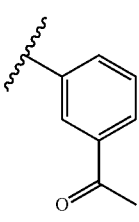 [SMILES: *c1cccc(C(C)=O)c1] | 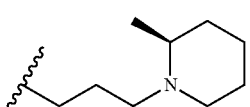 | H |

-continued
| Compound | R¹ | R² | R³ |
|---|---|---|---|
| 9 | 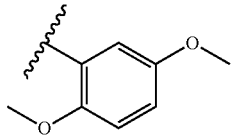 | 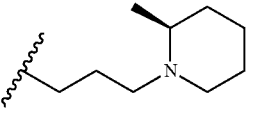 [SMILES: *CCCN1CCCC[C@@H]1C] | H |
| 10 | 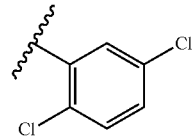 | 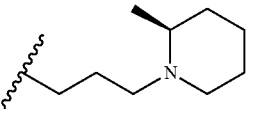 [SMILES: *CCCN1CCCC[C@@H]1C] | OCH₃ |
| 11 | 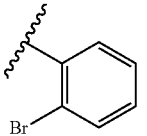 [SMILES: *c1ccccc1Br] | 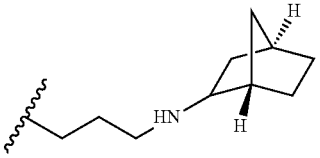 [SMILES: *CCCNC1C[C@@H]2CC[C@H]1C2] | H |
| 12 | 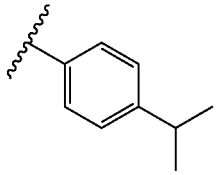 | 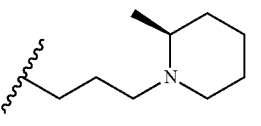 [SMILES: *CCCN1CCCC[C@@H]1C] | H |
| 13 | 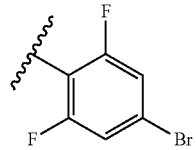 [SMILES: *c1c(F)cc(Br)cc1F] | 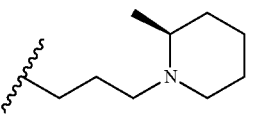 [SMILES: *CCCN1CCCC[C@@H]1C] | H |
| 14 | 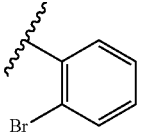 [SMILES: *c1ccccc1Br] | 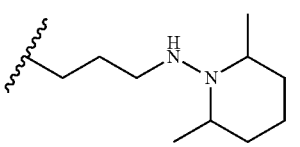 [SMILES: *CCCNN1C(C)CCCC1C] | H |
| 15 | 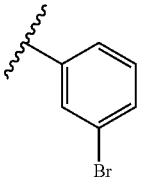 [SMILES: *c1cccc(Br)c1] | 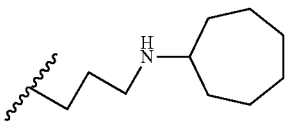 [SMILES: *CCCNC1CCCCCC1] | H |
| 16 | 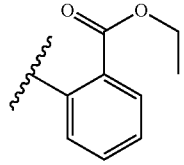 [SMILES: *c1ccccc1C(=O)OCC] | 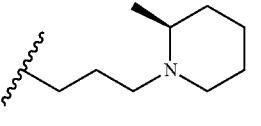 [SMILES: *CCCN1CCCC[C@@H]1C] | OH |
| 17 | 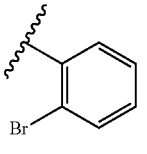 [SMILES: *c1ccccc1Br] | 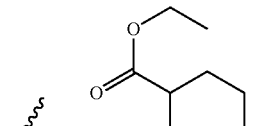 | H |

-continued

| Compound | R¹ | R² | R³ |
|---|---|---|---|
| 18 | 2-Br-phenyl | -(CH₂)₃-NH-(2-hydroxycyclohexyl) | H |
| 19 | 2-Br-phenyl | -(CH₂)₃-NH-(4-hydroxycyclohexyl) | H |
| 20 | 3,4-diCl-phenyl | -CH₂-phenyl | H |
| 21 | 4-isopropyl-phenyl | -(CH₂)₃-piperidinyl | H |
| 22 | 3-Br-phenyl | -(CH₂)₃-piperidinyl | H |

Pharmaceutical Composition

The disclosure provides in another embodiment a pharmaceutical composition comprising a compound of Formula I or Formula IA or pharmaceutically acceptable salt thereof and a pharmaceutically acceptable carrier. In some embodiments, the composition further contains, in accordance with accepted practices of pharmaceutical compounding, one or more additional therapeutic agents, pharmaceutically acceptable excipients, diluents, adjuvants, stabilizers, emulsifiers, preservatives, colorants, buffers, flavor imparting agents.

In one embodiment, the pharmaceutical composition comprises a compound selected from those illustrated in the table above or a pharmaceutically acceptable salt, thereof, and a pharmaceutically acceptable carrier.

The pharmaceutical composition of the present disclosure is formulated, dosed, and administered in a fashion consistent with good medical practice. Factors for consideration in this context include the particular disorder being treated, the particular subject being treated, the clinical condition of the subject, the cause of the disorder, the site of delivery of the agent, the method of administration, the scheduling of administration, and other factors known to medical practitioners.

The "therapeutically effective amount" of a compound or a pharmaceutically acceptable salt thereof that is administered is governed by such considerations, and is the minimum amount necessary to exert a cytotoxic effect on a cancer, or to inhibit protease activity, or both. Such amount may be below the amount that is toxic to normal cells, or the subject as a whole. Generally, the initial therapeutically effective amount of a compound (or a pharmaceutically acceptable salt, stereoisomer, or tautomer thereof) of the present disclosure that is administered is in the range of about 0.01 to about 200 mg/kg or about 0.1 to about 20 mg/kg of patient body weight per day, with the typical initial range being about 0.3 to about 15 mg/kg/day. Oral unit dosage forms, such as tablets and capsules, may contain from about 0.1 mg to about 1000 mg of a compound (or a pharmaceutically acceptable salt, stereoisomer, or tautomer thereof) of the present disclosure. In another embodiment, such dosage forms contain from about 50 mg to about 500 mg of a compound (or a pharmaceutically acceptable salt, stereoisomer, or tautomer thereof) of the present disclosure. In yet another embodiment, such dosage forms contain from about 25 mg to about 200 mg of a compound (or a pharmaceutically acceptable salt, stereoisomer, or tautomer thereof) of the present disclosure. In still another embodiment, such dosage forms contain from about 10 mg to about 100 mg of a compound (or a pharmaceutically acceptable salt, stereoisomer, or tautomer thereof) of the present disclosure. In a further embodiment, such dosage forms contain from about 5 mg to about 50 mg of a compound (or a pharmaceutically acceptable salt, stereoisomer, or tautomer thereof) of the present disclosure. In any of the foregoing embodiments the dosage form can be administered once a day or twice per day.

The compositions of the present disclosure can be administered orally, topically, parenterally, by inhalation or spray or rectally in dosage unit formulations. The term parenteral as used herein includes subcutaneous injections, intravenous, intramuscular, intrasternal injection or infusion techniques.

Suitable oral compositions as described herein include without limitation tablets, troches, lozenges, aqueous or oily suspensions, dispersible powders or granules, emulsion, hard or soft capsules, syrups or elixirs.

In another aspect, also encompassed are pharmaceutical compositions suitable for single unit dosages that comprise a compound of the disclosure or its pharmaceutically acceptable stereoisomer, salt, or tautomer and a pharmaceutically acceptable carrier.

The compositions of the present disclosure that are suitable for oral use may be prepared according to any method known to the art for the manufacture of pharmaceutical compositions.

For instance, liquid formulations of the compounds of the present disclosure contain one or more agents selected from the group consisting of sweetening agents, flavoring agents, coloring agents and preserving agents in order to provide pharmaceutically palatable preparations of the protease inhibitor.

For tablet compositions, a compound of the present disclosure in admixture with non-toxic pharmaceutically acceptable excipients is used for the manufacture of tablets. Examples of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions, a compound of the present disclosure is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending a compound of the present disclosure in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide a compound of the present disclosure in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the present disclosure may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation reaction products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, an aqueous suspension or an oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula I or Formula IA may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compositions for parenteral administrations are administered in a sterile medium. Depending on the vehicle used and concentration the concentration of the drug in the formulation, the parenteral formulation can either be a suspension or a solution containing dissolved drug. Adjuvants such as local anesthetics, preservatives and buffering agents can also be added to parenteral compositions.

Method of Use

The disclosure also provides, in an embodiment, a method for treating hepatitis C virus in a subject suffering therefrom, comprising administering to the subject a therapeutically effective amount of a compound of Formula I or Formula IA or pharmaceutically acceptable salt thereof.

Identification of a druggable binding pocket on HCV NS3/4A. HCV NS3/4 protease inhibitors that are approved or in clinical trials are effective against the wildtype GT1 strain, but mutations close to $S_2$ and $S_4$ pockets, namely Q80K/R, R123K, R155K/Q, 156T, D168A/V/G, or 1170T[30,31,35] significantly reduce efficacy of these drugs. The X-ray crystal structure of NS3/4A from wtGT1a strain shows that the pocket conformation is relatively stable in part due to inter-sidechain interactions between Arg155, Asp168, and Arg123. The side chains of R155 and D168 provide a substrate-friendly surface for the $P_2$ moiety of peptidomimetic protease inhibitors[14-15]. Therefore, mutations of either of these amino acids affect $P_2$-$S_2$ interactions and drug binding[32]. X-ray crystal structures of R155K/Q, 156T or D168A/V/G mutants clearly illustrates this mechanism[14]. In particular, the D168A mutation occurs frequency in viruses that have been treated with inhibitors that bind to $S_2$ or an adjacent $S_4$ patch. This mutation reduces efficacy of drugs such as the linear inhibitor, asunaprevir, $P_1$-$P_3$ macrocyclic compounds (danoprevir, simeprevir, paritaprevir), and $P_2$-$P_4$ macrocycle compounds (vaniprevir, grazoprevir)[28-29, 33-35].

Since the $S_2$ and $S_4$ pockets are known as multidrug resistance sites, our goal was to discover a new class of small molecule inhibitors that bind to the active site of HCV protease but have no interactions with the $S_2$ and $S_4$ pockets. A model based on high resolution co-crystal structure of HCV NS3/4A GT1a/GT3a protease (PDB code: 5EQR)24 was mutated to the wild type sequence (L1321, Q168D), converted to fully protonated models and optimized. The selection of HCV NS3/4A crystal structure as the docking simulation receptor was based on high resolution, well-defined active site, and small number of the outlier residues in the target pocket. The obtained models were used for virtual ligand screenings[8,26-27] with Molsoft ICM software against the structures of approximately 26,000 compounds that are available at the UC San Diego Center for Discovery and Innovation in Parasitic Diseases (CDIPD).

For each compound, the Gibbs free energy for interaction with the active site of HCV was calculated[8] and these ICM docking scores were ranked. Docking scores were only calculated for compounds that interact with the catalytic triad of His87, Asp87, and Ser 39 and with nearby residues. By setting the threshold of ICM docking score at −32 (arbitrary units), we discovered three classes of compounds that have strong binding potential to the active site of the target enzyme (FIG. 1). Within these classes, related compounds had consistent docking poses. For class A molecules, we discovered five compounds with docking scores ranging from −38 to −32 (supplementary table 1). These molecules consist of N-phenylsulfonamide of aminosulfonamide and were predicted to interact with the $S_1$, $S_2$ and $S_3$ pockets. For class B molecules, 2 compounds with docking scores ranging from −34 to −32 were discovered (supplementary table 2). These compounds bind to the active site of HCV protease in a different orientation to the class A molecules and primarily interact with $S_1$, $S_3$ and $S_4$. They consist of phenyl imidazolidine or phenyl triazolidine. The docking pose of compounds from these two classes show interactions with either the $S_2$ pocket (class A) or the $S_4$ pocket (class B) and therefore are not ideal compounds for perusing biochemical and cell based studies using a protease with mutations in both the $S_2$ and $S_4$ pockets.

Class C molecules contain a tryptophan derivative scaffold that bind in a different orientation to the class A and class B molecules. Importantly, the 14 molecules in this class (1-14) do not interact with the $S_2$ and $S_4$ pockets of HCV protease. They primarily bind to the $S_1$ and $S_3$ pockets (FIG. 1) and have docking scores ranging from −32 to −38. Within the 26,000-member compound library, we discovered 5 additional compounds that were structurally similar to members of the class C group (15-19) however their docking scores were below the −32 cut-off. We decided to include these compounds for our downstream cell-based studies. In addition, we searched libraries of commercially available compounds for class C-related structures. From this search, we found that ZINC2282531 had high structural similarity and an impressive docking score of −40. There are no available biological test results on this compound on the record. For our studies, we named this compound as analog 20 (Table 1).

Figure 3:
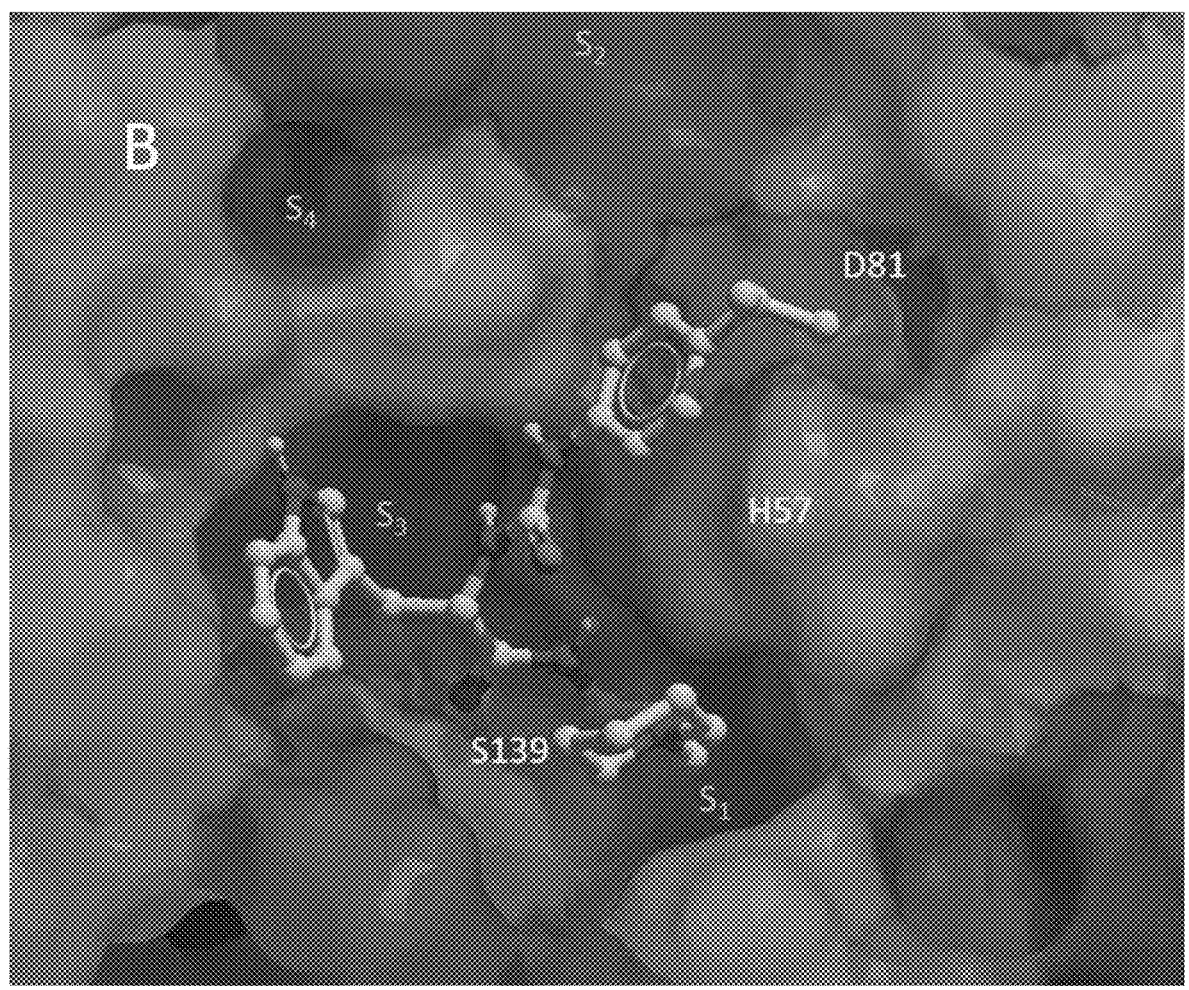
FIG. 3. Structural modelling of compound 22 in HCV NS3/4A active site. 3D docking pose of compound 22 in active site of HCV GT1a NS3/4A wild-type the labeled residues inside the pockets are represented by green blue and grey ovals. Sub-pockets are represented by yellow circles. Hydrogen bonding interactions between compound 22 and the corresponding residues (blue) are shown as dashed line. Binding mode of 22 (white) in the HCV GT1a NS3/4A crystal structure represented by multicolor skin (PDB code 5EQR)[24].

One important feature of this class of compounds is the ureido functional group that connects the core structure and $R_1$ group. A bi-dentate bond between the two secondary amines of the ureido group with the carbonyl oxygen of Arg155 backbone (FIG. 3B) stabilizes the ligand-enzyme interaction. In GT1a drug resistance mutants such as R155K and D168A, there are no salt bridges between an Arg155, Asp168, and Arg123 triad, thus additional backbone stabilization of Arg155 may be needed for a strong binding of the inhibitor to the mutant. Docking poses of superimposed structures of 20 compounds in NS3/4 GT1a (Figure S1) shows consistency of binding modes among the compounds in this class. Substituted $R_2$ and indole groups of class C compounds, are predicted to have interaction in $S_1$ and $S_3$ sub-pockets, main targeted pocket, in HCV protease active site. In addition, the His57 residue is involved in Pi-stacking (3.78 Å) interaction with the substituted aromatic rings in $R_1$ for all 20 inhibitors.

The 20 compounds from class C were tested in vivo for inhibition of viral replication (GT1b wild-type) in BM4-5 FEO cells and for mammalian cell cytotoxicity. The numbers of virus particles were evaluated by quantifying luciferase produced during the virus life cycle[41] while toxicity was evaluated using a cell viability assay. For viral replication, the 48 h $EC_{50}$ of these compounds ranged from 0.64 µM to 63.44 µM (Table IA) while the 48 h cell toxicity ranged from 2.24 µM to more than 100 µM. Prior to additional biochemical studies, several key chemical properties for each of the Class C molecules were determined. Calculated polar surface area (PSA), lipophilicity (LogP), and molecular weight for each compound (Table IA) complied with the general criteria for drug-like molecules.

Table IA Inhibition of viral replication ($EC_{50}$) in the HCV replicon assay for GT1b WT selected 20 compounds with the same chemical scaffold suggested by a docking screen. The compounds are labeled from 1 to 20. For each compound the R groups are shown along with $EC_{50}$, median lethal concentration at 50% ($LC_{50}$) for BM4-5 human liver cells, and three calculated descriptors.

TABLE 1A

Inhibition of viral replication ($EC_{50}$) in the HCV replicon assay for GT1b WT selected 20 compounds with the same chemical scaffold suggested by a docking screen. The compounds are labeled from 1 to 20. For each compound the R groups are shown along with $EC_{50}$, median lethal concentration at 50% ($LC_{50}$) for BM4-5 human liver cells, and three calculated descriptors.

| Compound | R₁ | R₂ | R₃ | ICM docking score[a] | $EC_{50} \pm SD$ (μM)[b] Gt 1b wt | $LC_{50} \pm SD$ (μM)[c] | Therapeutic Index[d] | Polar surface area (Å²) | Lipophilicity (LogP) |
|---|---|---|---|---|---|---|---|---|---|
| 1 | 3-Br-phenyl | 2-methylpiperidinyl-butyl | H | −38 | 0.95 ± 0.26 | 23.52 ± 1.89 | 24.73 | 71.05 | 5.10 |
| 2 | 2,5-diCl-phenyl | 2-methylpiperidinyl-butyl | F | −37 | 6.12 ± 2.30 | 6.94 ± 1.09 | 1.13 | 70.35 | 5.83 |
| 3 | 3,5-dinitro-phenyl | 2-methylpiperidinyl-butyl | H | −37 | 14.54 ± 0.51 | 36.82 ± 13.58 | 2.53 | 137.8 | 5.59 |
| 4 | 2,4,5-triCl-phenyl | 2-methylpiperidinyl-butyl | H | −36 | 0.87 ± 0.11 | 10.94 ± 3.099 | 12.57 | 70.35 | 6.16 |
| 5 | 3-SMe-phenyl | 4-phenylpiperazinyl | H | −36 | 4.78 ± 0.40 | >100 | >20.92 | 63.27 | 4.50 |
| 6 | 4-NMe₂-phenyl | 2-methylpiperidinyl-butyl | H | −35 | 63.44 ± 10.990 | >100 | >1.58 | 74.41 | 4.37 |
| 7 | 2,5-diCl-phenyl | 2-methylpiperidinyl-butyl | CH₃ | −35 | 6.35 ± 1.11 | 35.74 ± 15.59 | 5.62 | 91.52 | 5.96 |
| 8 | 3-acetyl-phenyl | 2-methylpiperidinyl-butyl | H | −34 | 10.92 ± 4.93 | >100 | >9.16 | 84.88 | 4.00 |

TABLE 1A-continued

Inhibition of viral replication (EC$_{50}$) in the HCV replicon assay for GT1b WT selected 20 compounds with the same chemical scaffold suggested by a docking screen. The compounds are labeled from 1 to 20. For each compound the R groups are shown along with EC$_{50}$, median lethal concentration at 50% (LC$_{50}$) for BM4-5 human liver cells, and three calculated descriptors.

| Compound | R$_1$ | R$_2$ | R$_3$ | ICM docking score[a] | EC$_{50}$ ± SD (μM)[b] Gt 1b wt | LC$_{50}$ ± SD (μM)[c] | Therapeutic Index[d] | Polar surface area (Å$^2$) | Lopophilicity (LogP) |
|---|---|---|---|---|---|---|---|---|---|
| 9 | | | H | −34 | 51.36 ± 15.20 | >100 | >1.95 | 85.53 | 4.31 |
| 10 | | | OCH$_3$ | −34 | 33.25 ± 3.17 | >100 | >3.03 | 70.35 | 5.65 |
| 11 | | | H | −34 | 5.99 ± 2.61 | 6.67 ± 1.56 | 1.11 | 95.18 | 5.26 |
| 12 | | | H | −33 | 1.50 ± 0.07 | 45.91 ± 13.01 | 30.61 | 71.05 | 5.37 |
| 13 | | | H | −33 | 35.36 ± 7.71 | 11.89 ± 1.79 | 0.34 | 78.65 | 5.40 |
| 14 | | | H | −32 | 5.15 ± 0.63 | 92.37 ± 45.25 | 17.94 | 94.32 | 4.55 |
| 15 | | | H | −26 | 6.82 ± 0.74 | 24.82 ± 0.58 | 3.64 | 77.9 | 5.88 |
| 16 | | | OH | −26 | 0.75 ± 0.07 | 2.24 ± 0.28 | 2.99 | 94.04 | 4.67 |

TABLE 1A-continued

Inhibition of viral replication (EC$_{50}$) in the HCV replicon assay for GT1b WT selected 20 compounds with the same chemical scaffold suggested by a docking screen. The compounds are labeled from 1 to 20. For each compound the R groups are shown along with EC$_{50}$, median lethal concentration at 50% (LC$_{50}$) for BM4-5 human liver cells, and three calculated descriptors.

| Compound | R$_1$ | R$_2$ | R$_3$ | ICM docking score[a] | EC$_{50}$ ± SD ($\mu$M)[b] Gt 1b wt | LC$_{50}$ ± SD ($\mu$M)[c] | Therapeutic Index[d] | Polar surface area (Å$^2$) | Lopophilicity (LogP) |
|---|---|---|---|---|---|---|---|---|---|
| 17 | 2-Br-phenyl | ethyl 1-butyl-piperidine-2-carboxylate | H | −24 | 2.98 ± 1.08 | 2.71 ± 0.11 | 0.91 | 79.36 | 4.60 |
| 18 | 2-Br-phenyl | 4-((2-hydroxycyclohexyl)amino)butyl | H | −20 | 4.58 ± 0.32 | 37.13 ± 7.95 | 8.11 | 71.05 | 4.36 |
| 19 | 2-Br-phenyl | 4-((4-hydroxycyclohexyl)amino)butyl | H | −16 | 32.63 ± 14.83 | >100 | >3.06 | 82.85 | 4.25 |
| 20 | 3,4-dichlorophenyl | benzyl | H | −40 | 14.51 ± 0.399 | >100 | >6.89 | 67.78 | 5.52 |

[a]Docking score calculated using ICM-Pro v3.8. [8, 27]
[b]HCV replicon assay
[c]CellTiter-Blue cell viability assay
[d]Therapeutic index is the ratio of LC$_{50}$/EC$_{50}$ The efficacy and toxicity of class C compounds were found to be diverse with the therapeutic index for antiviral activity relative to cell toxicity ranging from 0.3 to 31. We were interested in pursuing biochemical studies for compounds 1 and 12, the two candidates with the highest therapeutic index. These compounds also have favorable predicted chemical properties, such as molecular weight, water solubility polar surface area and permeability within an acceptable range for a drug-like molecule.

Design of New Compounds for Improved Binding to HCV Protease

Figure 4:
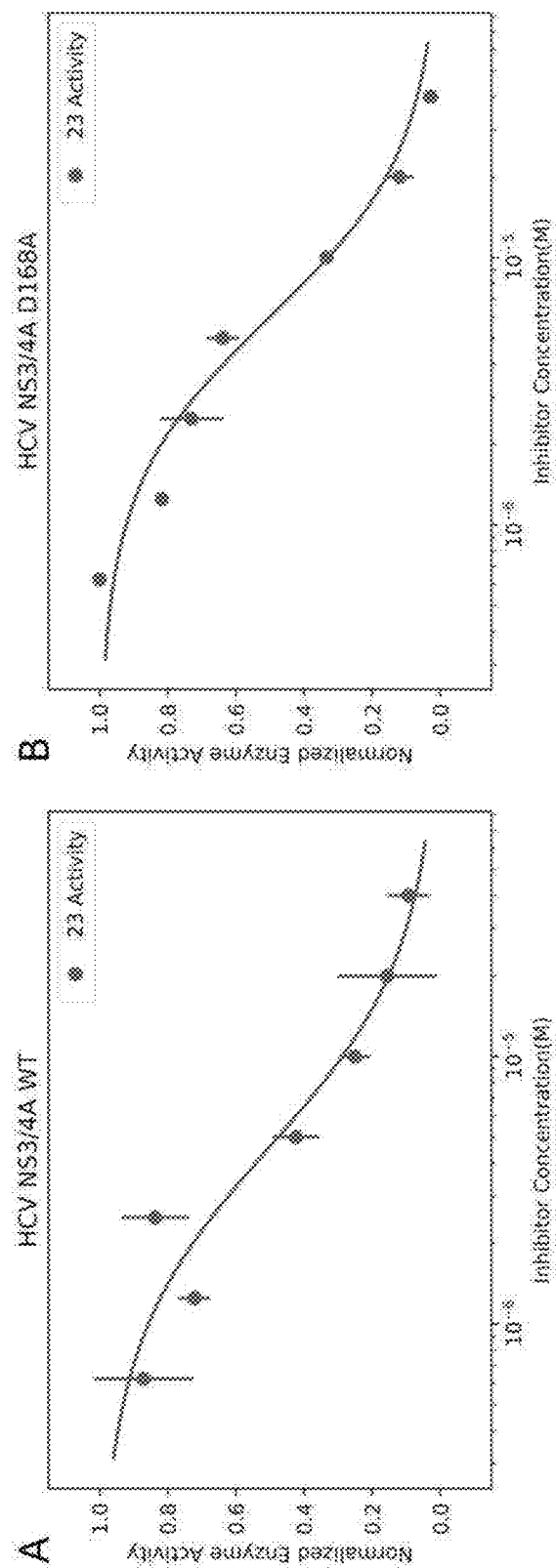
FIG. 4. HCV NS3/4A protease inhibition assay. Dose response curve of 22 with HCV protease GT1b WT (A) and D168A mutant (B) derived from the relative fluorescence absorption that represents the concentration of the cleavage products of fluorogenic peptide substrate (Ac-Glu-Glu-Val-Val-Ala-Cys-AMC) at 60 µM by GT1b WT protease, or by the D168A mutant in the presence of 5 at inhibitor concentrations between 0.625 to 40; the errors calculated from three measurements at each concentration.

In compounds 1 and 12, the R$_2$ functional group consists of 1-propyl-2-methyl-piperidine. Based on the predicted docking poses, removal of the methyl group was expected to improve the interaction between the catalytic triad and adjacent residues in HCV protease active site. Therefore, we designed analogs of compounds 1 and 12 that lacked the methyl group at R$_2$ and called them compounds 21 and 22, respectively (FIG. 4A). The docking score of 21 was unchanged from 1 (both −38) while the docking score of 22 was slightly better than 12 (−33 vs −34) (Table 2). The lowest energy binding pose of compound 22 in the active site of HCV NS3/4A is shown on FIG. 4B.

The following non-limiting examples illustrate additional embodiments of the present disclosure.

EXAMPLES

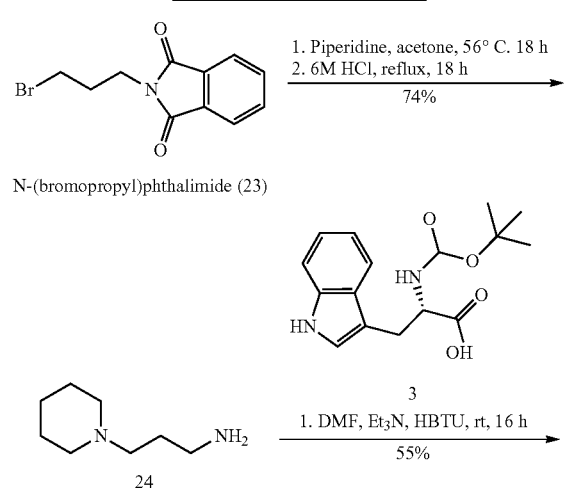

Scheme 1. Snythesis of 21 and 22

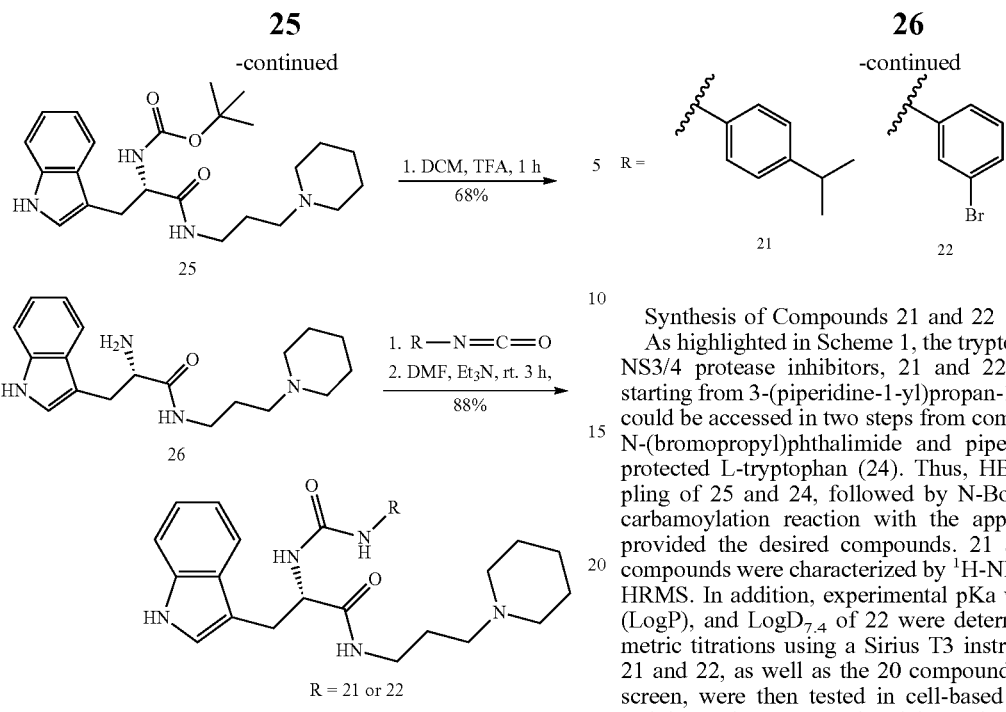

Synthesis of Compounds 21 and 22

As highlighted in Scheme 1, the tryptophan derived HCV NS3/4 protease inhibitors, 21 and 22, were synthesized starting from 3-(piperidine-1-yl)propan-1-amine (23), which could be accessed in two steps from commercially available N-(bromopropyl)phthalimide and piperidine, and N-Boc protected L-tryptophan (24). Thus, HBTU mediated coupling of 25 and 24, followed by N-Boc deprotection and carbamoylation reaction with the appropriate isocyanate provided the desired compounds. 21 and 22. These test compounds were characterized by $^1$H-NMR, $^{13}$C-NMR, and HRMS. In addition, experimental pKa values, lipophilicity (LogP), and LogD$_{7.4}$ of 22 were determined via potentiometric titrations using a Sirius T3 instrument. Compounds 21 and 22, as well as the 20 compounds from the primary screen, were then tested in cell-based assays to evaluate activity against HCV and toxicity to the host cells (Table 2).

TABLE 2

Inhibition of viral replication (EC$_{50}$) in the HCV replicon assay for GT1b wt by two synthesized compounds (21, 22). For each compound the R groups are shown along with EC$_{50}$, median lethal dose (LC$_{50}$) for BM4-5 human liver cells, and three calculated descriptors.

| Compound | Structure | ICM docking score[a] | EC$_{50}$ ± SD (μM)[b] Gt 1b wt | LC$_{50}$ ± SD (μM)[c] | Therapeutic Index[d] | Polar surface area (Å$^2$) | Lopophilicity (LogP) |
|---|---|---|---|---|---|---|---|
| 21 | 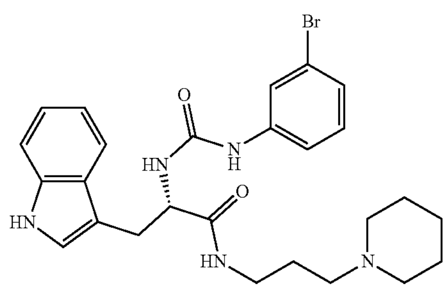 [SMILES: O=C(Nc1cccc(Br)c1)N[C@@H](Cc1c[nH]c2ccccc12)C(=O)NCCCN1CCCCC1] | −38 | 1.30 ± 1.25 | 29.52 ± 1.48 | 22.72 | 71.6 | 4.93 |
| 22 | 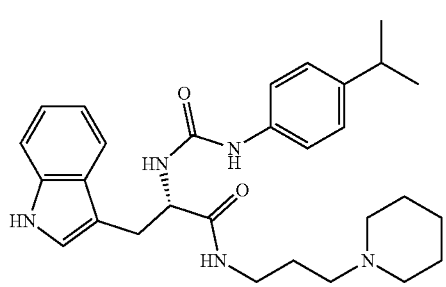 [SMILES: CC(C)c1ccc(NC(=O)N[C@@H](Cc2c[nH]c3ccccc23)C(=O)NCCCN2CCCCC2)cc1] | −34 | 0.64 ± 0.13 | 46.97 ± 6.98 | 73.39 | 71.6 | 5.19 (4.1)[e] |

[a]Docking score calculated using ICM-Pro v3.8.[8, 27]
[b]HCV replicon assay
[c]CellTiter-Blue cell viability assay
[d]Therapeutic index is the ratio of LC$_{50}$/EC$_{50}$
[e]Experiment value of logP Evaluation of Compounds in Viral Replication Assays and HCV Protease Activity Assays.

Compounds 21 and 22 were evaluated in the HCV replicon assay and for cytotoxicity using BM4-5 FEO cells. Compound 21 had slightly weaker anti-viral activity than 1 but also slightly improved cytotoxicity, therefore the therapeutic index was unchanged for these two analogs. The $IC_{50}$ value for compound 22 was 2-fold more potent than the related compound 12 and the cytotoxicity was unchanged. Therefore the therapeutic index for 22 improved 2-fold over 12 from 30.6 to 73.4.

In order to validate that this group of molecules elicit their cellular effects via inhibition of the viral protease, we incubated compounds 1, 12 and 22 with recombinant NS3/4A protease GT1b and an inhibitor-resistant mutant containing a D168A mutation. D168 is located in the $S_2$ and $S_4$ sub-pockets and mutations in these sub-pockets can cause significant resistance to the inhibitors resulting in decreased activity of peptidomimetic inhibitors[21,37-38]. Enzyme activity was evaluated using a fluorogenic peptide substrate, Ac-Glu-Glu-Val-Val-Ala-Cys-AMC, that has previously been described as a HCV protease substrate[43]. No enzyme assays were performed with compound 21 because it showed no improvement in anti-viral activity or selectivity when compared to the parent molecule, 1. As a control, potency was evaluated using the approved HCV protease inhibitor, simeprevir.

TABLE 3

NS3/4A Inhibitory assay of compounds 1, 12, and 22. The identified compounds inhibit both the wild type and the D168A mutant form of protease at similar $IC_{50}$ values.

| Compound | $IC_{50}$ (µM) GT1b WT | $IC_{50}$ (µM) GT1b D168A | $IC_{50}$_D168A/$IC_{50}$_wt ratio |
|---|---|---|---|
| 1 | 14.68 ± 1.23 | 11.37 ± 0.45 | 0.8 |
| 12 | 13.08 ± 2.77 | 11.45 ± 0.55 | 0.9 |
| 22 | 4.60 ± 1.26 | 5.98 ± 0.43 | 1.4 |
| Simeprevir | 0.043 ± 0.79 | 0.247 ± .39 | 5.7 |

HCV protease was incubated with 0.625 to 40 µM of compound 1, 12, and 22 $IC_{50}$ values were calculated. These studies show that wt protease activity is directly inhibited by compounds derived from the tryptophan scaffold. The potency of compound 22 was 120-fold lower than simeprevir ($IC_{50}$ 5.2 µM vs 0.043 µM) (Table 3) however, when inhibition was evaluated using the D168A mutant, potency of simeprevir decreased by 5.7-fold while no significant reduction on potency was calculated for compound 22. Likewise, compounds 1 and 12 that showed high efficiency and acceptable toxicity profile from the HCV replicon assay were assayed with wt and mutant HCV protease and found to have no significant change in potency. Therefore, our initial prediction that these tryptophan containing inhibitors do not interact with the $S_2$ and $S_4$ sub-pockets is likely to be correct. Other HCV protease inhibitors, such as Glecaprevir, Paritaprevir and Grazoprevir have been shown that have 4-fold to 154-fold reduced potency in cell-based assays when comparing the wild-type viruses with viruses that have a mutation at D168[39].

Figure 5:
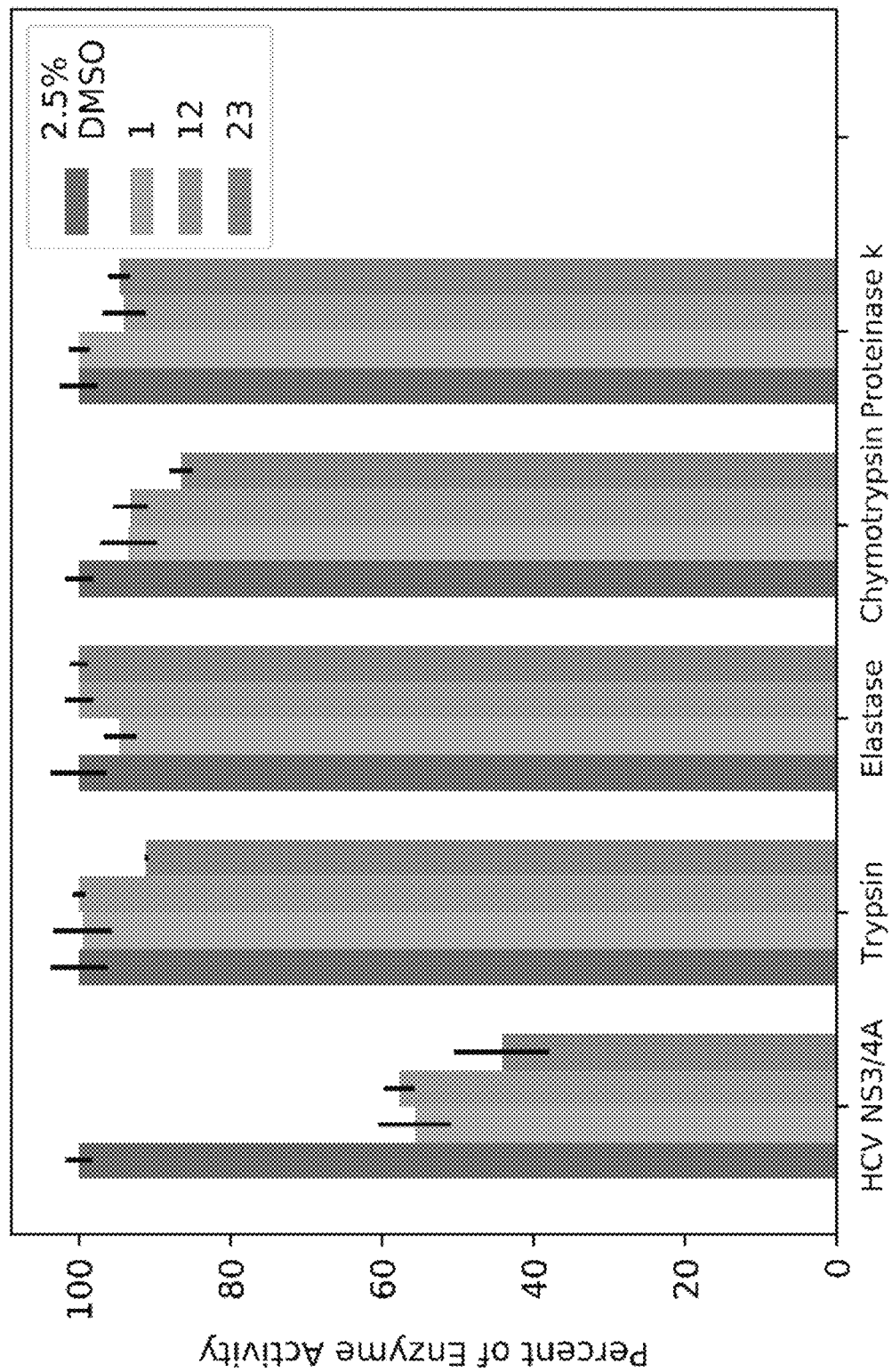
FIG. 5. Counter screening of top three compounds. Counter-screening on of 22, 1, and 13 at 5.20, 13.08 and 14.68 µM, respectively, to 40 nM concentration of HCV NS3/4A, trypsin, elastase, chymotrypsin, and proteinase show high HCV-NS3-specificity of 22, 1 and 12 inhibitors.
Figure 6:
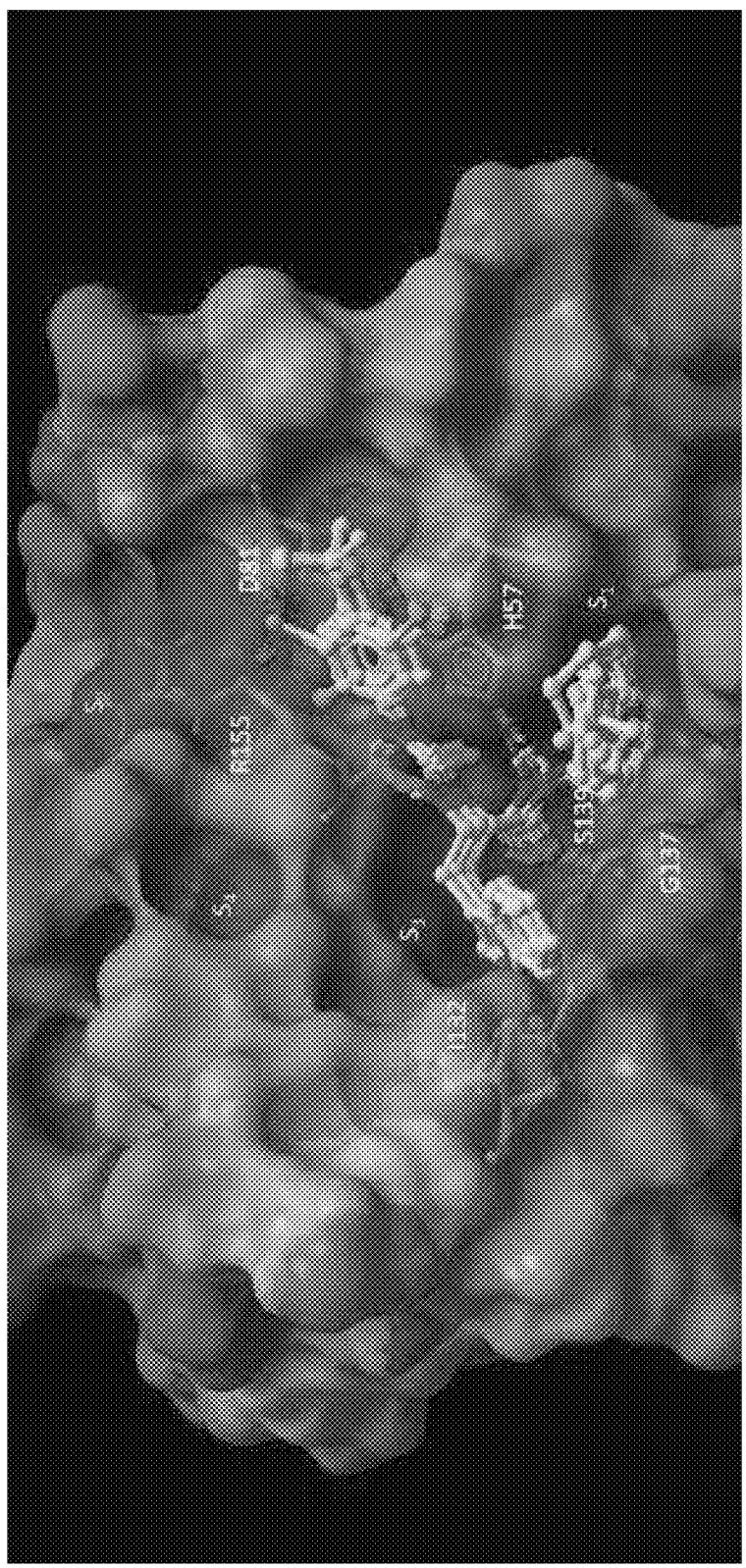
FIG. 6. Docking superposition of class C compounds in 5EQR HCV GT1a NS3/4A crystal structure (multicolor skin). The hydrogen bonding interaction are shown as dashed green and orange lines. The lowest-score poses of all compounds have the same binding mode.
Figure 7:
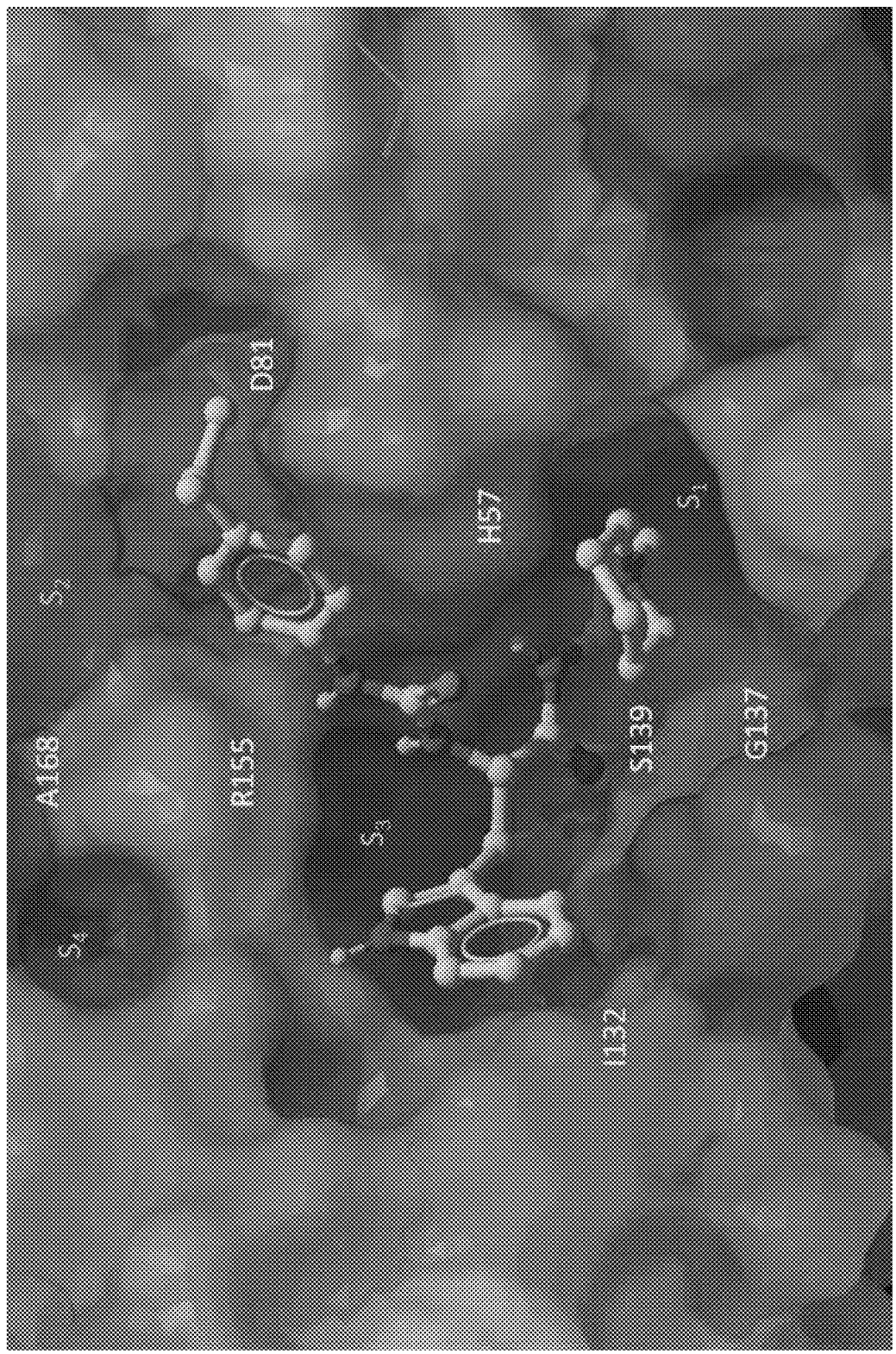
FIG. 7. The lowest score docking pose of compound 22 (yellow) in 5EQR HCV GT1a NS3/4A (multicolor skin) mutant D168A and hydrogen bonding interaction are shown as dashed green and orange lines. The best docking poses of 22 in both structures have similar conformations indicating consistent inhibitory activity in HCV NS3/4A protease both wild-type and double mutant D168A. An interaction diagram of compound 22 in active site of HCV GT1a NS3/4A mutant D168A, the labeled residues inside the pockets are represented by green blue and grey ovals. Sub-pockets are represented by yellow circles. Hydrogen bonding interactions between compound 22 and the corresponding residues (blue) are shown as dashed line.
Figure 8:
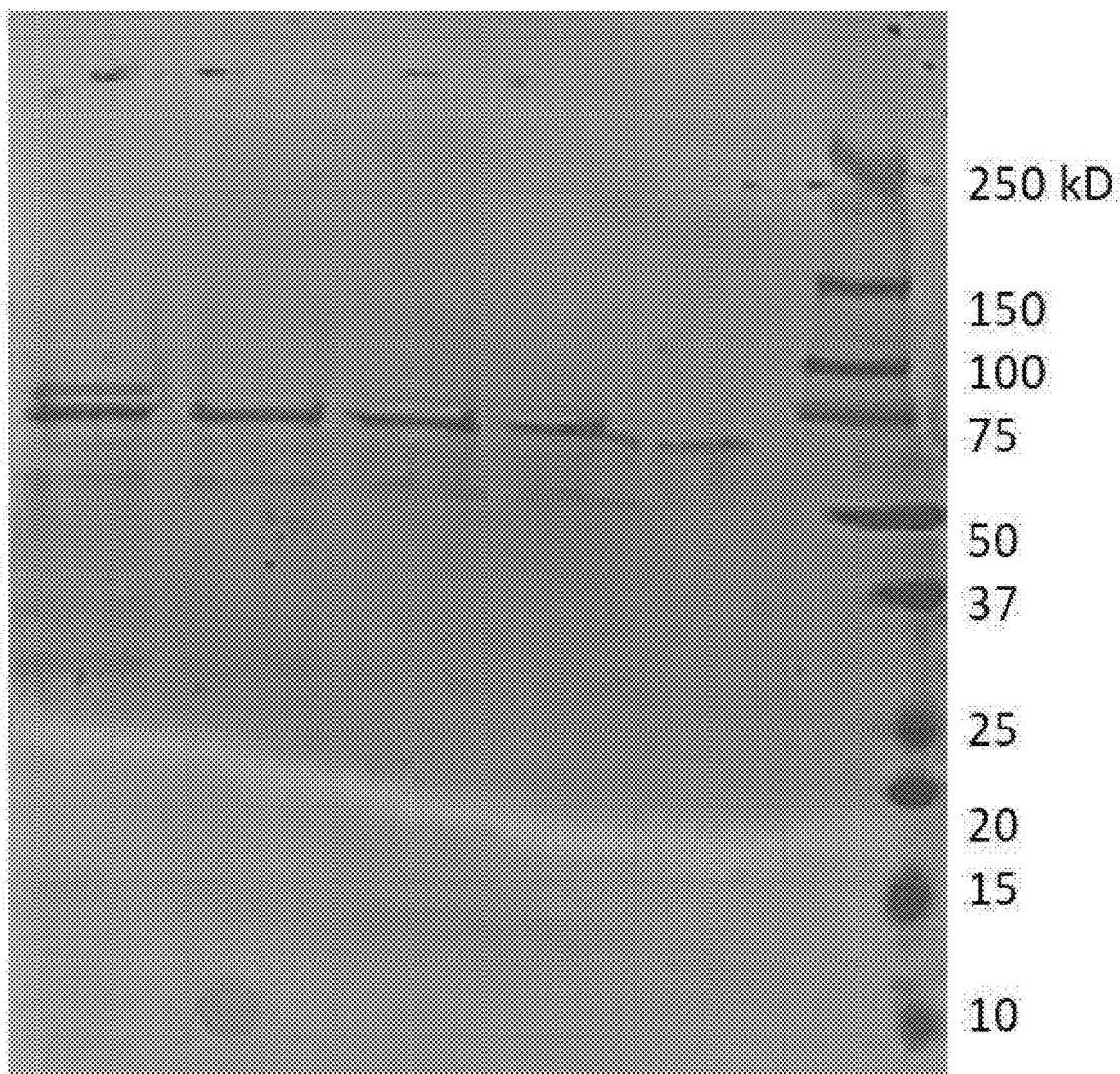
FIG. 8. SDS PAGE of purified NS3/4A protein. The SDS PAGE shows band (lanes 1 to 5 are corresponding to purified sample fraction 1, 3, 5, 7, and 9, respectively) assigned as HCV NS3/4A protein at 73.7 kDa.

To determine if compounds 1, 12, and 22 inhibit host serine proteases, we assayed these analogs with trypsin, elastase and chymotrypsin at a concentration that corresponds to the calculated $IC_{50}$ value that were obtained using the wt HCV protease. In addition, we tested these compounds for inhibition against the fungal serine protease, proteinase K that is structurally related to several mammalian serine proteases such as the proprotein convertase enzymes and furin[44]. Using a concentration of 40 nM for each enzyme, we found that 13.08 and 14.68, 5.2 µM of 1, 12, and 22, respectively did not decrease activity of trypsin, elastase, chymotrypsin and proteinase K significantly, while, at this concentration, these three compounds decreased HCV NS3/4A activity ranging between 40 to 60% (FIG. 5). Taken together, these data indicate that compounds with the tryptophan scaffold were selective from the viral protease over other serine proteases.

General Experimental. All solvents were reagent grade. All reagents were purchased from Aldrich or Fisher Scientific and used as received. Compound 20 was purchased from ZINC (ID: ZINC2282531). Thin layer chromatography (TLC) was performed with 0.25 mm E. Merck pre-coated silica gel plates. Silica gel column chromatography was performed with silica gel 60 (particle size 0.040-0.062 mm) supplied by Silicycle and Sorbent Technologies. TLC spots were detected by viewing under a UV light (254 nm). Proton ($^1$H) and carbon ($^{13}$C) NMR spectra were recorded on a 600 MHz Bruker Avance Ill spectrometer. Chemical shifts were reported relative to the residual solvent's peak. High-resolution mass spectra were measured using Thermo LCQdeca-MS. Unless otherwise stated, all final compounds were found to be >95% pure as determined by HPLC/MS and NMR.

3-(piperidine-1-yl)propan-1-amine (23). To a stirring solution of piperidine (1 g, 11.74 mmol) in acetone (11 mL), N-(bromopropyl)phthalimide (0.739 g, 2.935 mmol) was added. The mixture was heated at 56° C. and stirred for 18 h. Then the solvent was evaporated obtaining a dark yellow powder, which was re-dissolved in ethyl acetate, washed with 2 M of $K_2CO_3$, and extracted with 2 M of HCl. The aqueous layer was adjusted to pH 11 and re-extracted with DCM. The solvent was evaporated and the resulting dark yellow brown crude was added with 6 M HCl (40 mL) and then heated to reflux for 18 h. The reaction mixture was then washed with DCM, added with NaOH to adjust the pH to 12, and extracted again with DCM. The organic layer was dried over sodium sulfate, filtered and evaporated under reduced pressure to obtain the desired product as a brown solid in and evaporated to get brown crude of intermediate 24 in 74% yield (0.309 g). $^1$H NMR (CDCl$_3$) δ (ppm) 2.752 (t, J=6.9 Hz, 2H), 2.363 (m, 6H), 1.663 (m, 2H), 1.660 (m, 6H), 1.451 (m, NH$_2$). MS for $C_8H_{19}N_2$[M+H$^+$]: 143.15.

Tert-butyl (3-(1H-indol-3-yl)-1-oxo-1-((3-(piperidin-1-yl)propyl)amino)propan-2-yl)carbamate (24). To a solution of $N_a$-(tert-Butoxycarbonyl)-L-tryptophan (0.643 g, 2.112 mmol) in anhydrous DMF (8 mL), HBTU (1.602 g, 4.225 mmol) and Et$_3$N (1.068 g, 10.56 mmol) were added, followed by a dropwise addition of 24 (0.309 g, 2.176 mmol) in DMF (1.6 mL). The reaction mixture was stirred at room temperature for 22 h. During the reaction the solution color changed from yellow to dark green in 2 h. The completion of the reaction was checked by TLC using 10% MeOH in DMSO as the solute. The reaction was quenched by addition of saturated aqueous solution of NaHCO$_3$, which caused the mixture to turn yellow with white cloudy precipitates. The aqueous layer was extracted with ethyl acetate. The organic layer was dried over sodium sulfate, filtered and evaporated under reduced pressure. Purification via silica gel column chromatography (15% MeOH in DCM) furnished the title compound in 26% yield (0.240 g). $^1$H NMR (CDCl$_3$) δ (ppm) 8.785 (s, 1H), 7.635 (d, J=6.6 Hz, 1H), 7.368 (d, J=6.6 Hz, 1H), 7.289 (s, 1H), 7.181 (t, J=7.8 Hz, 1H), 7.112 (t, J=7.2 Hz, 1H), 7.082 (s, 1H), 4.410 (t, J=3.6 Hz, 1H), 3.332 (d, J=13.2 Hz, 2H), 3.186 (t, J=6.0 Hz, 2H), 2.245 (m, 4H), 2.193 (t, J=6.0 Hz, 2H), 1.510 (m, 4H), 1.453 (s, 9H), 1.402 (m, 2H). $^{13}$C NMR (CDCl$_3$) δ (ppm) 171.697, 155.378, 136.217, 127.648, 123.339, 122.066, 119.514, 119.042, 111.232, 110.551, 79.830, 57.225, 55.454, 54.148, 38.980, 28.906, 28.885, 25.130, 24.206, 23.755. MS for C$_{24}$H$_{36}$N$_4$O$_3$[M+H$^+$]: 429.29.

2-Amino-3-(1H-indol-3-yl)-N-(3-(piperidin-1-yl)propyl) propanamide (25). To a solution of 25 (50 mg, 0.17 mmol) in DCM (1.6 mL), a dropwise addition of TFA (0.35 mL) was made and the resulting mixture was stirred for 1 h. Evaporation of volatiles under reduced pressure followed by trituration in diethyl ether furnished the desired compounds in 88% (51 mg, 0.15 mmol) as a brown powder. $^1$H NMR (MeOD) δ (ppm), 8.484 (s, NH$_2$), 7.641 (d, J=7.8 Hz, 1H), 7.413 (d, J=7.4 Hz, 1H), 7.263 (s, 1H), 7.168 (t, J=7.2 Hz, 1H), 7.091 (t, J=7.2 Hz, 1H), 4.127 (t, J=4.2 Hz, 1H), 3.334 (d, J=12 Hz, 4H), 3.209 (dq, J=6.6, 23.4 Hz, 2H), 2.687 (m, 4H) 1.881 (m, 2H), 1.747 (m, 2H), 1.488 (m, 4H), $^{13}$C NMR (MeOD) δ (ppm) 169.233, 136.632, 127.073, 124.126, 121.485, 118.886, 117.888, 111.262, 106.881, 53.866, 52.875, 52.684, 36.036, 27.186, 23.372, 22.759, 21.202 MS for C$_{24}$H$_{36}$N$_4$O$_3$ [M+H$^+$]: 329.23.

2-(3-(3-bromophenyl)ureido)-3-(1H-indol-3-yl)-N-(3-(piperidin-1-yl)propyl)propenamide (21). To a solution of 26 (50 mg, 0.1166 mmol) in DMF (1.17 mL) and the solution was added by 3-Bromophenyl isocyanate (20.98 mg, 0.106 mmol). The reaction was started by adding the catalyst Et$_3$N (32.4 mg, 0.318 mmol), followed by stirring for 3 h, then solution turned yellow. The reaction was quenched by adding water (12 mL), extracted by ethyl acetate (4×15 mL), and washed by water (15 mL). The organic layer was purified by column chromatography (10-15% MeOH in DCM). Solvent was evaporated to obtain the remaining powder of 6 at yield 79% (44 mg, 0.084 mmol) $^1$H NMR (CDCl$_3$) δ (ppm), 8.498 (s, NH), 8.235 (s, NH), 7.607 (d, J=7.8 Hz, 1H), 7.561 (s, 1H), 7.290 (m, 1H), 7.198 (d, J=7.2 Hz, 1H), 7.101 (m, 5H), 6.976 (s, NH), 4.656 (d, J=6.6 Hz, 1H), 3.207 (m, 4H), 2.228 (m, 2H), 2.144 (m, 2H), 1.497 (m, 4H), 1.395 (p, J=6 Hz, 4H) 1.292 (m, 2H) $^{13}$C NMR (CDCl$_3$) δ (ppm), 173.145, 155.411, 140.939, 136.149, 130.102, 127.498, 125.092, 125.061, 123.505, 122.450, 122.021, 121.799, 119.472, 118.724, 117.460, 111.277, 110.411, 57.546, 55.300, 54.324, 40.017, 29.812, 25.865, 24.165 MS for C$_{26}$H$_{32}$BrN$_5$O$_2$ [M+H$^+$]: 526.18.

3-(1H-Indol-3-yl)-2-(3-(4-isopropylphenyl)ureido)-N-(3-(piperidin-1-yl)propyl)propenamide (22). To a solution of 26 (51 mg, 0.1189 mmol) in DMF (1.2 mL) and the solution was added by 4-isopropylphenyl isocyanate (17.4 mg, 0.108 mmol) was added, followed by an addition of catalytic amount of Et$_3$N (32.8 mg, 0.324 mmol). The reaction mixture was stirring for 3 h at rt during which tie, the solution turned yellow. The reaction was quenched by adding water (12 mL), extracted with ethyl acetate (4×15 mL). The combined organic layers were then washed with water (15 mL), dried over sodium sulfate, filtered and evaporated under reduced pressure. Purification via silica gel column chromatography (15% MeOH in DCM) to furnish the title compound in 66% yield (35 mg, 0.070 mmol). $^1$H NMR (CDCl$_3$) δ (ppm), 9.071 (s, NH), 8.311 (s, NH), 7.898 (s, NH), 7.635 (d, J=12 Hz, 1H), 7.290 (m, 3H), 7.103 (t, J=7.2 Hz, 1H), 7.036 (m, 4H), 6.960 (s, NH), 3.244 (s, 2H), 3.116 (d, J=27 Hz, 2H), 2.825 (t, J=6.6 Hz, 1H), 2.217 (m, 1H), 2.128 (m, 4H), 1.466 (m, 4H), 1.364 (d, J=9 Hz, 4H), 1.291 (s, 2H), 1.214 (d, J=6.6 Hz, 6H), $^{13}$C NMR (CDCl$_3$) δ (ppm) 173.287, 156.011, 142.890, 137.097, 136.162, 127.616, 126.690, 123.636, 121.781, 119.664, 119.245, 118.900, 118.866, 111.243, 110.503, 57.079, 55.240, 54.155, 39.333, 33.456, 29.765, 29.512, 25.561, 24.521, 24.171. MS for C$_{29}$H$_{39}$N$_5$O$_2$[M+H$^+$]: 490.32.

Replicon construct. The BM4-5 replicon is a sub-genomic HCV GT1b replicon that contains adaptive mutation of serine in the NS5A region[41]. The firefly luciferase gene was added into the BM4-5 replicon to generate BM4-5 FEO replicon. The construction procedures have been previously described[42].

Luciferase antiviral efficacy and cells viability assays. BM4-5 FEO replicon approximately 10,000 cells in 100 μL of medium were seeded into 96-well plates and incubate for 6 h for attachment. Then, the compounds were added at to the wells in specific concentration and incubate for 48 h. The luciferase assay (Bright-Glo; Promega) was carried out according to the manufacturer's instructions. Luciferase activity was determined using a microplate luminometer (Veritas microplate luminometer; Turner Biosystems). For cells viability assays, BM4-5 FEO at the density 10,000 cells in 100 μL medium was incubated at 37° C. for 6 h for attachment, then the compounds were added and incubated for another 48 hours. The number of living cells were measured by Cell Titer-blue assay (Promega). The fluorescence absorption (560$_{Ex}$/590$_{Em}$) for 96-well plate was read by Benchmark Scientific MR9600 with. The activity and toxicity of each compound were measured by at least six different concentrations in triplicate.

Plasmid construction and purification of HCV NS3/A protein. Drug resistant mutant D168A was generated by mutagenesis using NS3-containing recombinant plasmid (pETDuet-1 Hepatis C Virus NS3/4A, a gift from Michael Johnson, Addgene plasmid #16196) as a template. The single mutation of aspartic acid (D) to alanine (A) was introduced by mutagenesis at position 168 using specific primers (Forward: 5'-GTTGC-CAAAGCCGTTGCTTTCGTTCCGGTGGAA-3' and Reverse: 5'-TTCCACCG-GAACGAAAGCAACGGCTTTGGCAAC-3'). The over expression and purification were preformed followed the method that previously described[43]. Rosetta 2(DE3) cells (Novagen) containing the modified recombinant plasmid with histidine tag were grown in Lysogeny Broth medium. The over expression was introduced by addition of Isopropyl β-D-1-thiogalactopyranoside (IPTG) to the final concentration of 0.5 mM and the bacteria were incubated at room temperature for 16 h. The cells pellet was lysed by sonication in buffer A (50 mM HEPES [pH 7.6], 500 mM NaCl, 20 mM imidazole, 5 mM β-mercaptoethanol (β-MCE), 0.2% Triton X-100, 15% glycerol, and protease inhibitor cocktail (Sigma-Aldrich)). The solution was passed through Ni-NTA column and washed by buffer B (50 mM HEPES, pH 7.6, 500 mM NaCl, 50 mM imidazole, 5 mM β-MCE, 0.2% Triton X-100, and 15% glycerol). The His-tag fused protein was eluted by buffer C (50 mM HEPES, pH 7.6, 500 mM of NaCl, 500 mM of imidazole, 5 mM β-MCE, 0.2% Triton X-100, and 15% glycerol) followed by dialysis using buffer (50 mM HEPES, pH 7.6 and 500 mM of NaCl). Purified NS3/4A protein was concentrated an d buffer exchanged into buffer D (50 mM HEPES, pH 7.6, 500 mM of NaCl, 5 mM β-MCE, 0.2% Triton X-100, and 50% glycerol) using a protein concentrator 10 k (Amicon®).

HCV NS3/4A enzymatic inhibition assay. The activities of two proteases (recombinant HCV NS3/4A GT1b WT and full-length HCV NS3/4A GT1b D168A) were measured using a fluorogenic substrate, Ac-Glu-Glu-Val-Val-Ala-Cys-AMC (Sigma-Aldrich) where AMC corresponds to 7-amino-4-methylcourmarin. Assays were performed in 50 mM HEPES pH 7.4, 15 mM NaCl, 0.01% Triton X-100, 10 mM DTT in a black 384-well microplate (BD Falcon). The final concentration of enzyme, substrate, and DMSO were 40 nM, 60 µM, and 2.5%, respectively in a total volume of 30 µL. Fluorescence was monitored at excitation and emission wavelengths of 360 nm and 460 nm in a Synergy™ HTX Multi-Mode Microplate Reader (BioTek). Data was visualized using Gen5™ Software (Biotek). The activity of enzyme was calculated from the change in relative fluorescence units (RFU) over time. For inhibition assays, compounds were pre-incubated with enzyme for 240 minutes prior to adding the enzyme/inhibitor mixture to the substrate. All assays were performed in triplicate wells.

Counter-screening assay. Counter-screening assays were performed with 40 nM of bovine trypsin (Sigma), pig pancreatic elastase (Sigma), human chymotrypsin and proteinase k and 60 µM of the appropriate fluorogenic substrates for trypsin, elastase, chymotrypsin, and proteinase K are Boc-Leu-Arg-Arg-AMC (trypsin), Me-Arg-Arg-Pro-Val-AMC (elastase) and Suc-Arg-Arg-Pro-Phe-AMC (chymotrypsin and proteinase K). Assays were performed in 50 mM HEPES pH 7.4, 15 mM NaCl, 0.01% Triton X-100 in black 96-well microplates (BD Falcon) at a final volume of 50 µL. The final concentration of DMSO in each well was 2.5%. Fluorescence was measured as outlined above.

Computational modelling. Docking screening was performed by docking in-house library of approximately 27,000 small molecules and ranked based on their docking scores which represent to Gibbs free energy[8,27]. The algorithm for conformational sampling 3D structures of ligands and pocket are generated randomly by Biased probability Monte Carlo (BPMC)[26]. All scoring function and pharmacokinetic properties prediction were performed by the method implemented in the ICM-Pro v3.8.

REFERENCES CITED IN THE DISCLOSURE

[1] S. Blach, S. Zeuzem, M. Manns, I. Altraif, A.-S. Duberg, D. H. Muljono, I. Waked, S. M. Alavian, M.-H. Lee, F. Negro, et al. 'Global prevalence and genotype distribution of hepatitis C virus infection in 2015: a modelling study', *Lancet Gastroenterol Hepatol*, 2 (2017), 161-176

[2] World Health Organization. *Global Hepatitis Report 2017; Geneva, Switzerland*, 2017.

[2] B. Hajarizadeh, J. Grebely, and G. J. Dore, 'Epidemiology and Natural History of HCV Infection', *Nat Rev Gastroenterol Hepatol*, 10 (2013), 553-62.

[3] A. Majumdar, M. T. Kitson, and S. K. Roberts, 'Systematic Review: Current Concepts and Challenges for the Direct-Acting Antiviral Era in Hepatitis C Cirrhosis', *Aliment Pharmacol Ther.* 43 (2016), 1276-92.

[4] Y. Chen, C. Yu, X. Yin, X. Guo, S. Wu, and J. Hou, 'Hepatitis C Virus Genotypes and Subtypes Circulating in Mainland China', *Emerg Microbes Infect*, 6 (2017), e95.

[5] X. Zhang, 'Direct Anti-Hcv Agents', *Acta Pharm Sin B*, 6 (2016), 26-31.

[6] G. M. Keating, 'Ledipasvir/Sofosbuvir: A Review of Its Use in Chronic Hepatitis C', *Drugs.* 75 (2015), 675-85.

[7] C. Sarrazin, and S. Zeuzem, 'Resistance to Direct Antiviral Agents in Patients with Hepatitis C Virus Infection', *Gastroenterology*, 138 (2010), 447-62.

[8] M. A. Neves, M. Totrov, and R. Abagyan, 'Docking and Scoring with 1 cm: The Benchmarking Results and Strategies for Improvement', *J Comput Aided Mol Des*, 26 (2012), 675-86.

[9] J. Apelt, X Ligneau, H. H. Pertz, J. M. Arrang, C. R. Ganellin, J. C. Schwartz, W. Schunack, and H. Stark, 'Development of a New Class of Nonimidazole Histamine H$_3$ Receptor Ligands with Combined Inhibitory Histamine N-Methyltransferase Activity', *J. Med. Chem*, 45 (2002), 1128-41.

[10] D. L. Wyles, K. A. Kaihara, and R. T. Schooley, 'Synergy of a Hepatitis C Virus (Hcv) Ns4a Antagonist in Combination with Hcv Protease and Polymerase Inhibitors', *Antimicrob Agents Chemother.* 52 (2008), 1862-4.

[11] E. J. Lawitz, W. D. O'Riordan, A. Asatryan, B. L. Freilich, T. D. Box, J. S. Overcash, S. Lovell, T. I. Ng, W. Liu, A. Campbell, C. W. Lin, B. Yao, and J. Kort, 'Potent Antiviral Activities of the Direct-Acting Antivirals Abt-493 and Abt-530 with Three-Day Monotherapy for Hepatitis C Virus Genotype 1 Infection', *Antimicrob Agents Chemother*, 60 (2015), 1546-55.

[12] S. A. Shiryaev S A, E. R. Thomsen, P. Cieplak, E. Chudin, A. V. Cheltsov, M. S. Chee, et al. 'New Details of HCV NS3/4A Proteinase Functionality Revealed by a High-Throughput Cleavage Assay', *PLoS ONE* 7 (2012), e35759.

[13] G. R. Foster, S. Pianko, A. Brown, D. Forton, R. G. Nahass, J. George, E. Barnes, D. M. Brainard, B. Massetto, M. Lin, B. Han, J. G. McHutchison, G. M. Subramanian, C. Cooper, K. Agarwal, and Boson Study Group, 'Efficacy of Sofosbuvir Plus Ribavirin with or without Peginterferon-Alfa in Patients with Hepatitis C Virus Genotype 3 Infection and Treatment-Expericnced Patients with Cirrhosis and Hepatitis C Virus Genotype 2 Infection', *Gastroenterology.* 149 (2015), 1462-70.

[14] D. I. Soumana, A. Ali, and C. A. Schiffer, 'Structural Analysis of Asunaprevir Resistance in HCV NS3/4A Protease', *ACS Chem Biol*, 9 (2014), 2485-90.

[15] A. Ali, C. Aydin, R. Gildemeister, K. P. Romano, H. Cao, A. Ozen, D. Soumana, A. Newton, C. J. Petropoulos, W. Huang, and C. A. Schiffer, 'Evaluating the Role of Macrocycles in the Susceptibility of Hepatitis C Virus Ns3/4a Protease Inhibitors to Drug Resistance', *ACS Chem Biol.* 8 (2013), 1469-78.

[16] C. Lin, C. A. Gates, B. G. Rao, D. L. Brennan, J. R. Fulghum, Y. P. Luong, J. D. Frantz, K. Lin, S. Ma, Y. Y. Wei, R. B. Perni, and A. D. Kwong, 'In Vitro Studies of Cross-Resistance Mutations against Two Hepatitis C Virus Serine Protease Inhibitors, Vx-950 and Biln 2061', *J Biol Chem*, 280 (2005), 36784-91.

[17] N. Kurt Yilmaz, R. Swanstrom, and C. A. Schiffer, 'Improving Viral Protease Inhibitors to Counter Drug Resistance', *Trends Microbiol*, 24 (2016), 547-57.

[18] M. Cubero, J. I. Esteban, T. Otero, S. Sauleda, M. Bes, R. Esteban, J. Guardia, and J. Quer, 'Naturally Occurring Ns3-Protease-Inhibitor Resistant Mutant 156t in the Liver of an Untreated Chronic Hepatitis C Patient', *Virology*, 370 (2008), 237-45.

[19] J. Vermehren, and C. Sarrazin, 'The Role of Resistance in Hcv Treatment', *Best Pract Res Clin Gastroenterol*, 26 (2012), 487-503.

[20] A. K. Belfrage, E. Abdurakhmanov, E. Akerblom, P. Brandt, H. Alogheli, J. Neyts, U. H. Danielson, and A. Sandstrom, 'Pan-Ns3 Protease Inhibitors of Hepatitis C Virus Based on an R(3)-Elongated Pyrazinone Scaffold', *Eur J Med Chem*, 148 (2018), 453-64.

[21] F. McPhee, J. Friborg, S. Levine, C. Chen, P. Falk, F. Yu, D. Hernandez, M. S. Lee, S. Chaniewski, A. K. Sheaffer, and C. Pasquinelli, 'Resistance Analysis of the Hepatitis C Virus Ns3 Protease Inhibitor Asunaprevir', *Antimicrob Agents Chemother*, 56 (2012), 3670-81.

[22] P. M. Scola, L. Q. Sun, A. X. Wang, J. Chen, N. Sin, B. L. Venables, S. Y. Sit, Y. Chen, A. Cocuzza, D. M. Bilder, S. V. D'Andrea, B. Zheng, P. Hewawasam, Y. Tu, J.

Friborg, P. Falk, D. Hernandez, S. Levine, C. Chen, F. Yu, A. K. Sheaffer, G. Zhai, D. Barry, J. O. Knipe, Y. H. Han, R. Schartman, M. Donoso, K. Mosure, M. W. Sinz, T. Zvyaga, A. C. Good, R. Rajamani, K. Kish, J. Tredup, H. E. Klei, Q. Gao, L. Mueller, R. J. Colonno, D. M. Grasela, S. P. Adams, J. Loy, P. C. Levesque, H. Sun, H. Shi, L. Sun, W. Warner, D. Li, J. Zhu, N. A. Meanwell, and F. McPhee, The Discovery of Asunaprevir (Bms-650032), an Orally Efficacious Ns3 Protease Inhibitor for the Treatment of Hepatitis C Virus Infection', *J Med Chem,* 57 (2014), 1730-52.

[23] Y. Jiang, S. W. Andrews, K. R. Condroski, B. Buckman, V. Serebryany, S. Wenglowsky, A. L. Kennedy, M. R. Madduru, B. Wang, M. Lyon, G. A. Doherty, B. T. Woodard, C. Lemieux, M. Geck Do, H. Zhang, J. Ballard, G. Vigers, B. J. Brandhuber, P. Stengel, J. A. Josey, L. Beigelman, L. Blatt, and S. D. Seiwert, 'Discovery of Danoprevir (Itmn-191/R7227), a Highly Selective and Potent Inhibitor of Hepatitis C Virus (Hcv) Ns3/4a Protease', *J Med Chem,* 57 (2014), 1753-69.

[24] Djadé I. Soumana, Nese Kurt Yilmaz, Akbar Ali, Kristina L. Prachanronarong, and Celia A. Schiffer, 'Molecular and Dynamic Mechanism Underlying Drug Resistance in Genotype 3 Hepatitis C Ns3/4a Protease', *Journal of the American Chemical Society,* 138 (2016), 11850-59.

[25] A. Geddawy, Y. F. Ibrahim, N. M. Elbahie, and M. A. Ibrahim, 'Direct Acting Anti-Hepatitis C Virus Drugs: Clinical Pharmacology and Future Direction', *J Transl Int Med,* 5 (2017), 8-17.

[26] R. Abagyan, and M. Totrov, 'Biased probability Monte Carlo conformational searches and electrostatic calculations for peptides and proteins', *J. Mol. Biol.* 235 (1994), 983-1002

[27] M. A. Neves, M. Totrov, and R. Abagyan, 'Docking and scoring with ICM: the benchmarking results and strategies for improvement', *J Comput Aided Mol Des.* 26 (2012), 675-686.

[28] B. L. Venables, N. Sin, A. X. Wang, L. Q. Sun, Y. Tu, D. Hernandez, A. Sheaffer, M. Lee, C. Dunaj, G. Zhai, D. Barry, J. Friborg, F. Yu, J. Knipe, J. Sandquist, P. Falk, D. Parker, A. C. Good, R. Rajamani, F. McPhee, N. A. Meanwell, and P. M. Scola, 'P3-P4 Ureas and Reverse Carbamates as Potent Hcv Ns3 Protease Inhibitors: Effective Transposition of the P4 Hydrogen Bond Donor', *Bioorg Med Chem Lett.* 28 (2018), 1853-59.

[29] Stéphane L. Bogen, Weidong Pan, Sumei Ruan, Latha G. Nair, Ashok Arasappan, Frank Bennett, Kevin X. Chen, Edwin Jao, Srikanth Venkatraman, Banclia Vibulbhan, Rong Liu, Kuo-Chi Cheng, Zhuyan Guo, Xiao Tong, Anil K. Saksena, Viyyoor Girijavallabhan, and F. George Njoroge, 'Toward the Back-up of Boceprevir (Sch 503034): Discovery of New Extended P4-Capped Ketoamide Inhibitors of Hepatitis C Virus Ns3 Serine Protease with Improved Potency and Pharmacokinetic Profiles', *Journal of Medicinal Chemistry.* 52 (2009), 3679-88.

[30] C. Sarrazin, and S. Zeuzem, 'Resistance to Direct Antiviral Agents in Patients With Hepatitis C Virus Infection', *Gastroenterology,* 132 (2010), 447-462.

[31] J. Vermehren, and C. Sarrazin, 'The role of resistance in HCV treatment', *Best Pract Res Clin Gastroenterol,* 26 (2012), 487-503

[32] Akbar Ali, Cihan Aydin, Reinhold Gildemeister, Keith P. Romano, Hong Cao, Ay$eg6l Ozen, Djade Soumana, Alicia Newton, Christos J. Petropoulos, Wei Huang, and Celia A. Schiffer, 'Evaluating the Role of Macrocycles in the Susceptibility of Hepatitis C Virus Ns3/4a Protease Inhibitors to Drug Resistance', *ACS Chemical Biology,* 8 (2013), 1469-78.

[33] M. P. Manns, E. Gane, M. Rodriguez-Torres, A. Stoehr, C. T. Yeh, P. Marcellin, R. T. Wiedmann, P. M. Hwang, L. Caro, R. J. Barnard, A. W. Lee, and M. K. Protocol 007 Study Group, 'Vaniprevir with Pegylated Interferon Alpha-2a and Ribavirin in Treatment-Naive Patients with Chronic Hepatitis C: A Randomized Phase Ii Study', *Hepatology,* 56 (2012), 884-93.

[34] M. P. Manns, M. Bourliere, Y. Benhamou, S. Pol, M. Bonacini, C. Trepo, D. Wright, T. Berg, J. L. Calleja, P. W. White, J. O. Stern, G. Steinmann, C. L. Yong, G. Kukolj, J. Scherer, and W. O. Boecher, 'Potency, Safety, and Pharmacokinetics of the Ns3/4a Protease Inhibitor Bi201335 in Patients with Chronic Hcv Genotype-1 Infection', *J Hepatol,* 54 (2011), 1114-22.

[35] E. S. Svarovskaia, R. Martin, J. G. McHutchison, M. D. Miller, and H. Mo, 'Abundant Drug-Resistant Ns3 Mutants Detected by Deep Sequencing in Hepatitis C Virus-Infected Patients Undergoing Ns3 Protease Inhibitor Monotherapy', *J Clin Microbiol,* 50 (2012), 3267-74.

[36] Keith P. Romano, Akbar Ali, William E. Royer, and Celia A. Schiffer, 'Drug Resistance against Hcv Ns3/4a Inhibitors Is Defined by the Balance of Substrate Recognition Versus Inhibitor Binding', *Proceedings of the National Academy of Sciences,* 107 (2010), 20986-91.

[37] J. Courcambeck, M. Bouzidi, R. Perbost, B. Jouirou, N. Amrani, P. Cacoub, G. Pépe, J.-M. Sabatier, and P. Halfon, 'Resistance of hepatitis C virus to NS3-4A protease inhibitors: mechanisms of drug resistance induced by R155Q, 156T, D168A and D168V mutations', *Antivir Ther,* 11 (2006), 847-55

[38] L. Lu, T. J. Pilot-Matias, K. D. Stewart, J. T. Randolph, R. Pithawalla, W. He, P. P. Huang, L. L. Klein, H. Mo, and A. Molla, 'Mutations Conferring Resistance to a Potent Hepatitis C Virus Serine Protease Inhibitor in Vitro', *Antimicrob Agents Chemother,* 48 (2004), 2260-6.

[39] T. I. Ng. R. Tripathi, T. Reisch, L. Lu, T. Middleton, T. A. Hopkins, R. Pithawalla, M. Irvin, T. Dekhtyar, P. Krishnan, G. Schnell, J. Beyer, K. F. McDaniel, J. Ma, G. Wang, L. J. Jiang, Y. S. Or, D. Kempf, T. Pilot-Matias, and C. Collins, 'In Vitro Antiviral Activity and Resistance Profile of the Next-Generation Hepatitis C Virus Ns3/4a Protease Inhibitor Glecaprevir', *Antimicrob Agents Chemother,* 62 (2018).

[40] K. P. Romano, A. Ali, C. Aydin, D. Soumana, A. Ozen, L. M. Deveau, C. Silver, H. Cao, A. Newton, C. J. Petropoulos, W. Huang, and C. A. Schiffer, 'The Molecular Basis of Drug Resistance against Hepatitis C Virus Ns3/4a Protease Inhibitors', *PLoS Pathog,* 8 (2012), e1002832.

[41] J. T. Guo, V. V. Bichko, and C. Seeger, 'Effect of Alpha Interferon on the Hepatitis C Virus Replicon', *J Virol,* 75 (2001), 8516-23.

[42] D. L. Wyles, K. A. Kaihara, F. Vaida, and R. T. Schooley, 'Synergy of Small Molecular Inhibitors of Hepatitis C Virus Replication Directed at Multiple Viral Targets', *J Virol,* 81 (2007), 3005-8.

[43] A. Po, 'Enzymatic Properties of Hepatitis C Virus NS3 Serine Protease and Bio-Engineering of Serine Protease Inhibitors (Serpins) Against the NS3 Protease and Elastase'. (Unpublished master's thesis). University of British Columbia, Vancouver, British Columbia, Camada

[44] C. Betzel, S. Gourinath, P. Kumar, P. Kaur, M. Perbandt, S. Eschenburg, and T. P. Singh, 'Structure of a Serine Protease Proteinase K from Tritirachium Album Limber at 0.98 a Resolution', *Biochemistry,* 40 (2001), 3080-8.

Supplementary Data

TABLE S1

Structure and ICM docking score of class A compounds. The compounds are labeled from A1 to A5.

| Compound | Structure | ICM docking score |
|---|---|---|
| A1 | 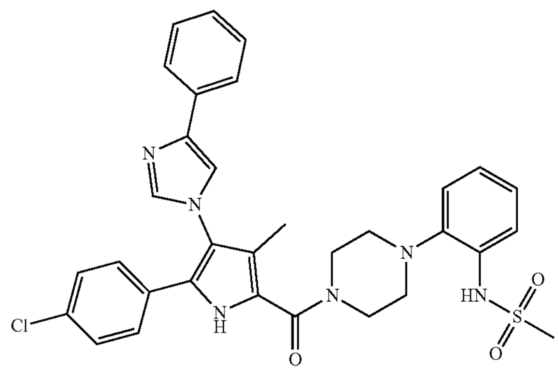 [SMILES: Cc1c(C(=O)N2CCN(c3ccccc3NS(C)(=O)=O)CC2)[nH]c(-c2ccc(Cl)cc2)c1-n1cnc(-c2ccccc2)c1] | −38 |
| A2 | 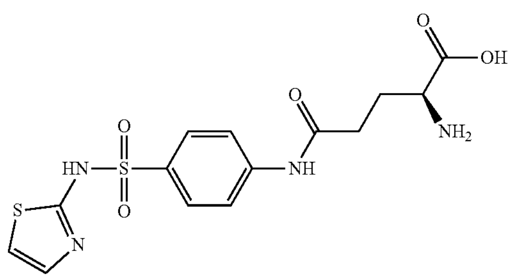 [SMILES: N[C@@H](CCC(=O)Nc1ccc(S(=O)(=O)Nc2nccs2)cc1)C(=O)O] | −38 |
| A3 | 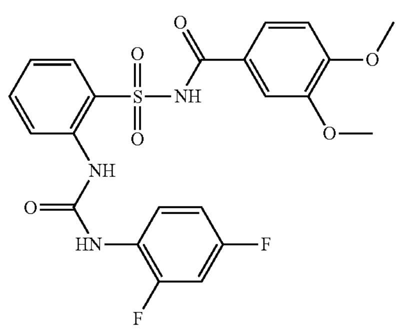 [SMILES: COc1ccc(C(=O)NS(=O)(=O)c2ccccc2NC(=O)Nc2ccc(F)cc2F)cc1OC] | −37 |
| A4 | 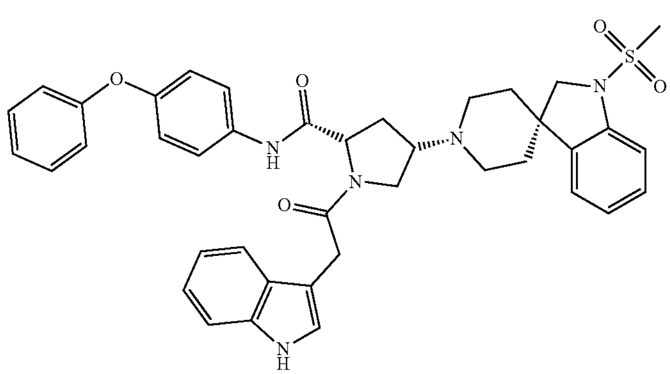 | −32 |

TABLE S1-continued

Structure and ICM docking score of class A compounds. The compounds are labeled from A1 to A5.

| Compound | Structure | ICM docking score |
|---|---|---|
| A5 | 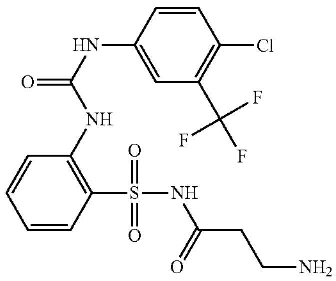 [SMILES: NCCC(=O)NS(=O)(=O)c1ccccc1NC(=O)Nc1ccc(Cl)c(C(F)(F)F)c1] | −32 |

TABLE 2

Structure and ICM docking score of class B compounds. The compounds are labeled from B1 to B2.

| Compound | Structure | ICM docking score |
|---|---|---|
| B1 | 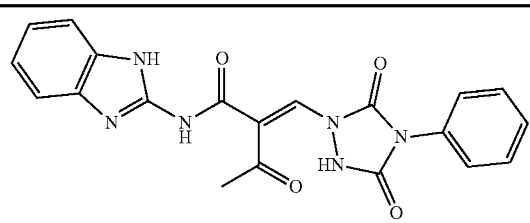 | −34 |
| B2 | 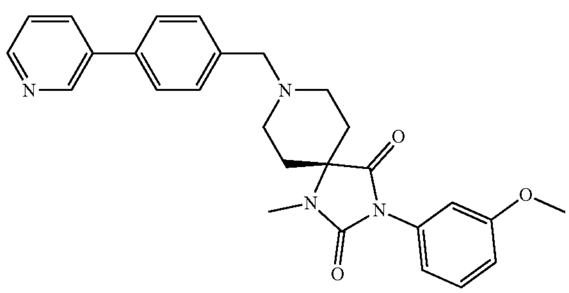 | −32 |

The invention claimed is:

1. A compound according to Formula I:

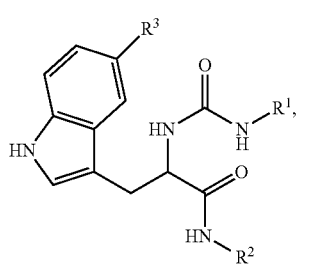

wherein $R^1$ is phenyl optionally substituted by one or more substituents independently selected from the group consisting of $C_1$-$C_6$-alkyl, $C_1$-$C_6$-alkoxy, —S($C_1$-$C_6$-alkyl), halo, —OH, —NO$_2$, —NRR', and —C(O)OR;

$R^2$ is —(CH$_2$)$_m$(NH)$_n$—(C$_6$-C$_{10}$-aryl), —(CH$_2$)$_m$(NH)$_n$-(3- to 14-membered heterocycloalkyl) (wherein 1-4 ring members are independently selected from N, O, and S), or —(CH$_2$)$_m$(NH)$_n$—(C$_3$-C$_{14}$-cycloalkyl);

wherein each aryl, heterocycloalkyl, and cycloalkyl are optionally substituted by one or more substituents independently selected from the group consisting of $C_1$-$C_6$-alkyl, $C_1$-$C_6$-alkoxy, —OH, —NRR', and C(O)OR;

$R^3$ is selected from the group consisting of H, $C_1$-$C_6$-alkyl, $C_1$-$C_6$-alkoxy, halo, and —OH, R and R' are independently selected from H and $C_1$-$C_6$-alkyl;

m is 3;

n is 0;

or a pharmaceutically acceptable salt thereof.

2. The compound according to claim 1, wherein the compound is a compound of Formula IA:

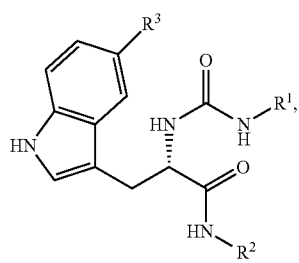

(IA)

or a pharmaceutically acceptable salt thereof.

3. The compound or pharmaceutically acceptable salt thereof according to claim 1, wherein R² is

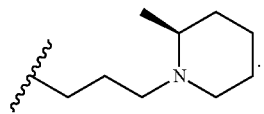 [SMILES: *CCCN1CCCC[C@@H]1C]

4. A compound according to Formula I:

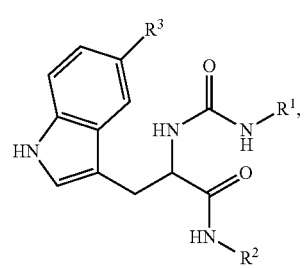

(I)

wherein R¹, R², and R³ are selected from the following table:

| Compound | R¹ | R² | R³ |
|---|---|---|---|
| 1 | 3-Br-phenyl | 4-(2-methylpiperidin-1-yl)butyl | H |
| 2 | 2,5-dichlorophenyl | 4-(2-methylpiperidin-1-yl)butyl | F |
| 3 | 3,5-dinitrophenyl | 4-(2-methylpiperidin-1-yl)butyl | H |
| 4 | 2,4,5-trichlorophenyl | 4-(2-methylpiperidin-1-yl)butyl | H |
| 5 | 3-(methylthio)phenyl | 4-phenylpiperazin-1-yl | H |

| Compound | R¹ | R² | R³ |
| --- | --- | --- | --- |
| 6 | 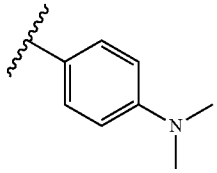 [SMILES: *c1ccc(N(C)C)cc1] | 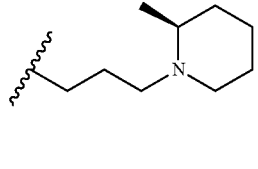 [SMILES: *CCCN1CCCC[C@@H]1C] | H |
| 7 | 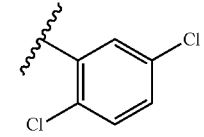 | 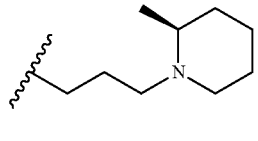 [SMILES: *CCCN1CCCC[C@@H]1C] | CH₃ |
| 8 | 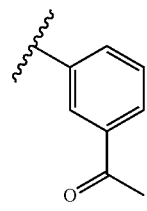 [SMILES: *c1cccc(C(C)=O)c1] | 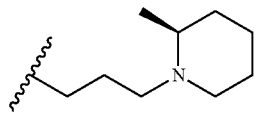 [SMILES: *CCCN1CCCC[C@@H]1C] | H |
| 9 | 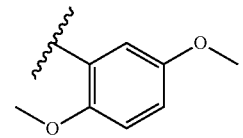 | 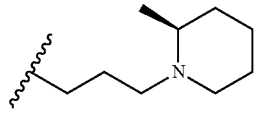 [SMILES: *CCCN1CCCC[C@@H]1C] | H |
| 10 | 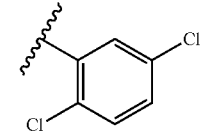 [SMILES: *c1cc(Cl)ccc1Cl] | 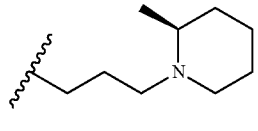 [SMILES: *CCCN1CCCC[C@@H]1C] | OCH₃ |
| 11 | 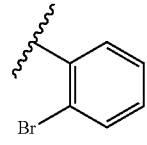 [SMILES: *c1ccccc1Br] | 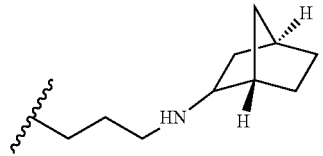 [SMILES: *CCCNC1C[C@@H]2CC[C@H]1C2] | H |
| 12 | 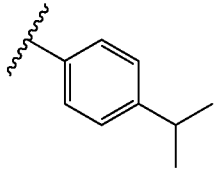 [SMILES: *c1ccc(C(C)C)cc1] | 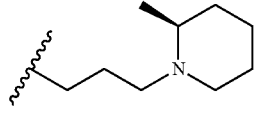 [SMILES: *CCCN1CCCC[C@@H]1C] | H |
| 13 | 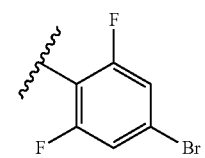 [SMILES: *c1c(F)cc(Br)cc1F] | 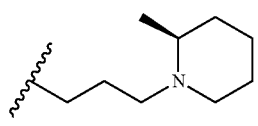 [SMILES: *CCCN1CCCC[C@@H]1C] | H |
| 14 | 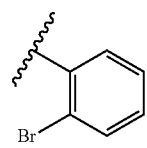 [SMILES: *c1ccccc1Br] | 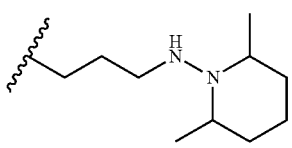 [SMILES: *CCCNN1C(C)CCCC1C] | H |

-continued

| Compound | R¹ | R² | R³ |
|---|---|---|---|
| 15 | 3-bromophenyl | -(CH₂)₃-NH-cycloheptyl | H |
| 16 | 2-(ethoxycarbonyl)phenyl | -(CH₂)₃-N(2-methylpiperidinyl) | OH |
| 17 | 2-bromophenyl | -(CH₂)₃-N(2-ethoxycarbonylpiperidinyl) | H |
| 18 | 2-bromophenyl | -(CH₂)₃-NH-(2-hydroxycyclohexyl) | H |
| 19 | 2-bromophenyl | -(CH₂)₃-NH-(4-hydroxycyclohexyl) | H |
| 20 | 3,4-dichlorophenyl | -CH₂-phenyl | H |
| 21 | 4-isopropylphenyl | -(CH₂)₃-piperidinyl | H |
| 22 | 3-bromophenyl | -(CH₂)₃-piperidinyl | H |

5. A pharmaceutical composition comprising a compound or pharmaceutically acceptable salt thereof according to claim 1 and a pharmaceutically acceptable carrier.

6. A method for treating hepatitis C virus in a subject suffering therefrom, comprising administering to the subject a therapeutically effective amount of a compound or pharmaceutically acceptable salt thereof according to claim 1.

\* \* \* \* \*